(12) United States Patent
Holmes et al.

(10) Patent No.: US 10,244,973 B2
(45) Date of Patent: Apr. 2, 2019

(54) SYSTEMS, DEVICES, AND METHODS FOR BODILY FLUID SAMPLE TRANSPORT

(71) Applicant: Theranos, Inc., Palo Alto, CA (US)

(72) Inventors: Elizabeth A. Holmes, Palo Alto, CA (US); Clarissa Lui, Palo Alto, CA (US); Michael Chen, Palo Alto, CA (US); Daniel Young, Palo Alto, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 15/160,196

(22) Filed: May 20, 2016

(65) Prior Publication Data

US 2017/0020425 A1 Jan. 26, 2017

Related U.S. Application Data

(63) Continuation of application No. 14/098,177, filed on Dec. 5, 2013, now Pat. No. 9,386,948.

(Continued)

(51) Int. Cl.
*A61B 5/00* (2006.01)
*A61B 5/15* (2006.01)
(Continued)

(52) U.S. Cl.
CPC ...... *A61B 5/150022* (2013.01); *A61B 5/1422* (2013.01); *A61B 5/1438* (2013.01);
(Continued)

(58) Field of Classification Search
CPC ............... A61B 5/1422; A61B 5/1438; A61B 5/150305; A61B 5/150343; A61B 5/15022; A61B 5/15074; A01N 1/02
See application file for complete search history.

(56) References Cited

U.S. PATENT DOCUMENTS 3,405,706 A 10/1968 Paul
3,604,410 A 9/1971 Whitacre
(Continued)

FOREIGN PATENT DOCUMENTS

CN 2128870 3/1993
CN 101533005 A 9/2009
(Continued)

OTHER PUBLICATIONS

Office Action dated Mar. 23, 2017 for U.S. Appl. No. 14/639,986.
(Continued)

*Primary Examiner* — Max Hindenburg

(57) ABSTRACT

Bodily fluid sample transport systems, devices, and method are provided. In at least one embodiment described herein, methods are provided for the physical transport of small volumes of bodily fluid in liquid form from one location to another location. By way of nonlimiting example, the samples are collected in liquid form at a collection site, transported in liquid form, and arrive at an analysis site in liquid form. In many embodiments, the liquid form during transport is not held in a porous matrix, wicking material, webbing, or similar material that prevents sample for being extracted in liquid form at the destination site. In one embodiment, small volume of sample in each sample vessel is in the range of about 1 ml to about 1 microliter.

19 Claims, 14 Drawing Sheets

Related U.S. Application Data

(60) Provisional application No. 61/733,886, filed on Dec. 5, 2012.

(51) Int. Cl.

| | | |
|---|---|---|
| *A61B 5/154* | (2006.01) | |
| *B01L 9/06* | (2006.01) | |
| *A61B 5/151* | (2006.01) | |
| *B01L 3/00* | (2006.01) | |
| *B65D 25/10* | (2006.01) | |
| *B65D 43/16* | (2006.01) | |
| *B65D 81/18* | (2006.01) | |

(52) U.S. Cl.
CPC ........ *A61B 5/1545* (2013.01); *A61B 5/15105* (2013.01); *A61B 5/150305* (2013.01); *A61B 5/150343* (2013.01); *A61B 5/150755* (2013.01); *A61B 5/150786* (2013.01); *B01L 3/5082* (2013.01); *B01L 9/06* (2013.01); *B65D 25/108* (2013.01); *B65D 43/16* (2013.01); *B65D 81/18* (2013.01); *A61B 5/15003* (2013.01); *A61B 5/15074* (2013.01); *A61B 5/150099* (2013.01); *A61B 5/150213* (2013.01); *A61B 5/150389* (2013.01); *A61B 5/150473* (2013.01); *A61B 5/150732* (2013.01); *B01L 2200/025* (2013.01); *B01L 2200/185* (2013.01); *B01L 2300/021* (2013.01); *B01L 2300/12* (2013.01); *B01L 2300/1822* (2013.01); *B01L 2300/1855* (2013.01); *B01L 2300/1894* (2013.01)

(56) References Cited

U.S. PATENT DOCUMENTS

| | | | |
|---|---|---|---|
| 3,848,581 A | 11/1974 | Cinqualbre et al. | |
| 3,960,139 A | 6/1976 | Bailey | |
| 4,150,089 A | 4/1979 | Linet | |
| 4,210,156 A | 7/1980 | Bennett | |
| 4,271,119 A | 6/1981 | Columbus | |
| 4,292,817 A | 10/1981 | Loucks | |
| 4,434,802 A | 3/1984 | Rilliet | |
| 4,453,927 A | 6/1984 | Sinko | |
| 4,474,033 A | 10/1984 | Baker | |
| 4,492,634 A | 1/1985 | Villa-Real | |
| 4,650,662 A | 3/1987 | Goldfinger et al. | |
| 4,676,256 A | 6/1987 | Golden | |
| 4,703,762 A | 11/1987 | Rathbone et al. | |
| 4,761,381 A | 8/1988 | Blatt et al. | |
| 4,844,098 A | 7/1989 | Mitchen | |
| 4,932,533 A | 6/1990 | Collier | |
| 4,949,722 A | 8/1990 | Bean et al. | |
| 4,951,685 A | 8/1990 | Blair | |
| 4,964,509 A | 10/1990 | Insley et al. | |
| 4,976,271 A | 12/1990 | Blair | |
| 4,980,297 A | 12/1990 | Haynes et al. | |
| 5,000,854 A | 3/1991 | Yang | |
| 5,008,059 A | 4/1991 | Kaeufer et al. | |
| 5,033,476 A | 7/1991 | Kasai | |
| 5,057,282 A | 10/1991 | Linder | |
| 5,086,780 A | 2/1992 | Schmitt | |
| 5,100,626 A | 3/1992 | Levin | |
| 5,104,375 A | 4/1992 | Wolf et al. | |
| 5,139,031 A | 8/1992 | Guirguis | |
| 5,145,565 A | 9/1992 | Kater et al. | |
| 5,199,795 A | 4/1993 | Russo et al. | |
| 5,222,502 A | 6/1993 | Kurose | |
| 5,249,584 A | 10/1993 | Karkar et al. | |
| 5,277,198 A | 1/1994 | Kanner et al. | |
| 5,314,412 A | 5/1994 | Rex | |
| 5,360,423 A | 11/1994 | McCormick | |
| 5,364,533 A | 11/1994 | Ogura et al. | |
| 5,447,417 A | 9/1995 | Kuhl et al. | |
| 5,505,721 A | 4/1996 | Leach et al. | |
| 5,569,210 A | 10/1996 | Moen | |
| 5,578,269 A | 11/1996 | Yaremko et al. | |
| 5,707,876 A | 1/1998 | Levine | |
| 5,785,662 A | 7/1998 | Alexander | |
| 5,833,057 A * | 11/1998 | Char ........................ B01L 9/06 |
| | | | 206/204 |
| 5,833,630 A | 11/1998 | Kloth | |
| 5,897,508 A | 4/1999 | Konrad | |
| 5,922,210 A | 7/1999 | Brody et al. | |
| 6,056,925 A | 5/2000 | Sarstedt | |
| 6,221,672 B1 | 4/2001 | Baugh et al. | |
| 6,344,326 B1 | 2/2002 | Nelson et al. | |
| 6,391,265 B1 | 5/2002 | Buechler et al. | |
| 6,521,460 B1 | 2/2003 | Strasser et al. | |
| 6,531,098 B1 | 3/2003 | Kenney | |
| 6,541,243 B1 | 4/2003 | Harris et al. | |
| 6,555,064 B2 | 4/2003 | Baugh et al. | |
| 6,555,066 B2 | 4/2003 | Baugh et al. | |
| 6,555,381 B2 | 4/2003 | Baugh et al. | |
| 6,569,676 B1 | 5/2003 | Tripp et al. | |
| 6,626,863 B1 | 9/2003 | Berler | |
| 6,662,941 B2 | 12/2003 | Lowry et al. | |
| 6,852,290 B2 | 2/2005 | Hager et al. | |
| 6,875,405 B1 | 4/2005 | Mathus et al. | |
| 6,899,672 B2 | 5/2005 | Mierisch | |
| 7,118,538 B2 | 10/2006 | Konrad | |
| 7,279,134 B2 | 10/2007 | Chan et al. | |
| 7,305,896 B2 | 12/2007 | Howell et al. | |
| 7,335,188 B2 | 2/2008 | Graf | |
| 7,378,054 B2 | 5/2008 | Karmali | |
| 7,413,910 B2 | 8/2008 | Kearney et al. | |
| 7,699,966 B2 | 4/2010 | Qin et al. | |
| 7,785,773 B1 | 8/2010 | Anderson et al. | |
| 7,810,348 B2 | 10/2010 | Shewchuk | |
| 8,158,062 B2 | 4/2012 | Dykes et al. | |
| 8,273,312 B2 | 9/2012 | Porat et al. | |
| 8,474,228 B2 | 7/2013 | Adair et al. | |
| 8,801,918 B2 | 8/2014 | Qin et al. | |
| 8,841,118 B2 | 9/2014 | Robinson et al. | |
| 9,224,120 B2 | 12/2015 | Grabiner et al. | |
| 9,386,948 B2 * | 7/2016 | Holmes ............ A61B 5/150305 |
| 2001/0031932 A1 | 10/2001 | Blake et al. | |
| 2002/0004647 A1 | 1/2002 | Leong | |
| 2002/0164779 A1 | 11/2002 | Cocola et al. | |
| 2003/0159999 A1 | 8/2003 | Oakey et al. | |
| 2003/0166291 A1 | 9/2003 | Jones et al. | |
| 2003/0185707 A1 | 10/2003 | Iwaki et al. | |
| 2003/0206828 A1 | 11/2003 | Bell | |
| 2004/0030353 A1 | 2/2004 | Schmelzeisen-Redeker et al. | |
| 2004/0051154 A1 | 3/2004 | Yamakawa et al. | |
| 2004/0053422 A1 | 3/2004 | Chan et al. | |
| 2004/0089057 A1 | 5/2004 | Hobbs et al. | |
| 2004/0129678 A1 | 7/2004 | Crowley et al. | |
| 2004/0191124 A1 | 9/2004 | Noetzel et al. | |
| 2004/0245102 A1 | 12/2004 | Gilbert et al. | |
| 2005/0036907 A1 | 2/2005 | Shoji | |
| 2005/0059163 A1 | 3/2005 | Dastane et al. | |
| 2005/0106066 A1 | 5/2005 | Saltsman et al. | |
| 2005/0139547 A1 | 6/2005 | Manoussakis et al. | |
| 2005/0232813 A1 | 10/2005 | Karmali | |
| 2005/0236346 A1 | 10/2005 | Whitney | |
| 2005/0243304 A1 | 11/2005 | Padmanabhan et al. | |
| 2006/0160243 A1 | 7/2006 | Tang et al. | |
| 2006/0228258 A1 | 10/2006 | Samsoondar | |
| 2006/0228259 A1 | 10/2006 | Samsoondar | |
| 2006/0233676 A1 | 10/2006 | Stein | |
| 2006/0254962 A1 | 11/2006 | Samsoondar | |
| 2007/0016102 A1 | 1/2007 | Askin | |
| 2007/0104616 A1 | 5/2007 | Keenan et al. | |
| 2007/0154895 A1 | 7/2007 | Spaid et al. | |
| 2007/0227967 A1 | 10/2007 | Sakaino et al. | |
| 2007/0269893 A1 | 11/2007 | Blankenstein et al. | |
| 2007/0272000 A1 | 11/2007 | Kahl et al. | |
| 2008/0025872 A1 | 1/2008 | Dykes et al. | |
| 2008/0076190 A1 | 3/2008 | Carlisle et al. | |
| 2008/0299663 A1 | 12/2008 | Hudson | |
| 2008/0312555 A1 | 12/2008 | Boecker | |
| 2008/0318259 A1 | 12/2008 | Ranby | |

(56) References Cited

U.S. PATENT DOCUMENTS

| | | |
|---|---|---|
| 2009/0047179 A1 | 2/2009 | Ping et al. |
| 2009/0053732 A1 | 2/2009 | Vermesh et al. |
| 2009/0088336 A1 | 4/2009 | Burd et al. |
| 2009/0107909 A1 | 4/2009 | Kotera et al. |
| 2009/0120865 A1 | 5/2009 | Chung et al. |
| 2009/0136386 A1 | 5/2009 | Duffy et al. |
| 2009/0136982 A1 | 5/2009 | Tang et al. |
| 2009/0139925 A1 | 6/2009 | Sternberg |
| 2009/0162941 A1 | 6/2009 | Winkler et al. |
| 2009/0181411 A1 | 7/2009 | Battrell et al. |
| 2009/0208923 A1 | 8/2009 | Gelfand et al. |
| 2009/0226957 A1 | 9/2009 | Paterlini-Brechot |
| 2009/0240165 A1 | 9/2009 | Yoneya et al. |
| 2009/0259145 A1 | 10/2009 | Bartfeld et al. |
| 2009/0306543 A1 | 12/2009 | Slowey et al. |
| 2010/0184056 A1 | 7/2010 | Weinberger et al. |
| 2010/0185322 A1 | 7/2010 | Bylsma et al. |
| 2010/0224551 A1 | 9/2010 | Hongo et al. |
| 2010/0249652 A1 | 9/2010 | Rush et al. |
| 2010/0261223 A1 | 10/2010 | Margraf et al. |
| 2010/0284861 A1 | 11/2010 | Horiike |
| 2011/0011781 A1 | 1/2011 | Blankenstein et al. |
| 2011/0124025 A1 | 5/2011 | Castracane et al. |
| 2011/0284110 A1 | 11/2011 | Gagnon |
| 2011/0294205 A1 | 12/2011 | Hukari et al. |
| 2011/0312481 A1 | 12/2011 | Nguyen et al. |
| 2012/0029384 A1 | 2/2012 | Crosman |
| 2012/0045826 A1 | 2/2012 | Yantz et al. |
| 2012/0085648 A1 | 4/2012 | Kartalov et al. |
| 2012/0101407 A1 | 4/2012 | Chan |
| 2012/0123297 A1 | 5/2012 | Brancazio |
| 2012/0141329 A1 | 6/2012 | Yamakawa et al. |
| 2012/0177537 A1 | 7/2012 | Aota et al. |
| 2012/0220047 A1 | 8/2012 | Seifried et al. |
| 2012/0256027 A1 | 10/2012 | Yang et al. |
| 2012/0258459 A1 | 10/2012 | Huang |
| 2012/0271123 A1 | 10/2012 | Castle et al. |
| 2012/0277629 A1 | 11/2012 | Bernstein et al. |
| 2012/0305500 A1 | 12/2012 | Bormann et al. |
| 2013/0019697 A1 | 1/2013 | McKeen et al. |
| 2013/0068310 A1 | 3/2013 | Sip et al. |
| 2013/0079248 A1 | 3/2013 | Kim et al. |
| 2013/0172780 A1 | 7/2013 | Kuenstner |
| 2013/0175213 A1 | 7/2013 | Dorrer et al. |
| 2013/0264205 A1 | 10/2013 | Hwang et al. |
| 2013/0264266 A1 | 10/2013 | Shick et al. |
| 2013/0264295 A1 | 10/2013 | Lee et al. |
| 2014/0004501 A1 | 1/2014 | Talebpour et al. |
| 2014/0073990 A1 | 3/2014 | Holmes et al. |
| 2014/0323911 A1 | 3/2014 | Sloan |
| 2014/0134595 A1 | 5/2014 | Kurowski et al. |
| 2014/0138260 A1 | 5/2014 | Briman |
| 2014/0171829 A1 | 6/2014 | Holmes et al. |
| 2014/0219886 A1 | 8/2014 | Choi et al. |
| 2014/0234949 A1 | 8/2014 | Wasson et al. |
| 2014/0316300 A1 | 10/2014 | Holmes et al. |
| 2014/0323913 A1 | 10/2014 | Holmes et al. |
| 2014/0339161 A1 | 11/2014 | Leonard et al. |
| 2014/0342371 A1 | 11/2014 | Holmes |
| 2014/0356884 A1 | 12/2014 | Mittal et al. |
| 2014/0358036 A1 | 12/2014 | Holmes |
| 2015/0060353 A1 | 3/2015 | Neijzen et al. |
| 2015/0192504 A1 | 7/2015 | Cho et al. |
| 2015/0231627 A1 | 8/2015 | Sloan et al. |
| 2016/0069918 A1 | 3/2016 | Holmes et al. |

FOREIGN PATENT DOCUMENTS

| | | |
|---|---|---|
| CN | 202376524 U | 8/2012 |
| EA | 200600893 A1 | 12/2006 |
| EP | 0203930 B1 | 7/1990 |
| EP | 0550950 A2 | 7/1993 |
| EP | 1005910 A2 | 6/2000 |
| EP | 2052807 A1 | 4/2009 |
| GB | 2375487 A | 11/2002 |
| GB | 2409411 | 6/2005 |
| JP | 07013304 | 3/1995 |
| JP | 2004184099 A | 7/2004 |
| JP | 2007167123 A | 7/2007 |
| SU | 1088789 A | 4/1984 |
| WO | 1986003008 A1 | 5/1986 |
| WO | 2005076733 A2 | 8/2005 |
| WO | 2005088300 A1 | 9/2005 |
| WO | 2005098431 A1 | 10/2005 |
| WO | 2009053432 A | 4/2009 |
| WO | 2011079217 A1 | 6/2011 |
| WO | 2012004704 A1 | 1/2012 |
| WO | 2012012779 A2 | 1/2012 |
| WO | 2014039909 A | 3/2014 |
| WO | 2014145330 A2 | 9/2014 |
| WO | 2014145935 A1 | 9/2014 |
| WO | 2014160903 A2 | 10/2014 |
| WO | 2014088606 | 7/2015 |
| WO | 2015134809 A1 | 9/2015 |

OTHER PUBLICATIONS

Office Action dated Mar. 28, 2017 for U.S. Appl. No. 14/629,069.
Office Action dated May 15, 2017 for U.S. Appl. No. 14/447,099.
Office Action dated May 5, 2017 for U.S. Appl. No. 14/214,771.
Advisory Action dated Sep. 28, 2016 for U.S. Appl. No. 14/629,069.
BD Diagnostics. product catalogue 2010/2011.
BIOSIGMA. Disposable Labware for Life Science. catalogue 2009.
International Search Report and Written Opinion dated Aug. 13, 2015 for PCT/US2015/019060.
International Search Report and Written Opinion dated Aug. 6, 2015 for PCT/US2015/020307.
Notice of Allowance dated Feb. 23, 2016 for U.S. Appl. No. 14/098,177.
Notice of Allowance dated Jun. 13, 2016 for U.S. Appl. No. 14/320,471.
Notice of Allowance dated Aug. 10, 2015 for U.S. Appl. No. 14/320,471.
Office Action dated Jan. 11, 2016 for U.S. Appl. No. 14/447,099.
Office Action dated Nov. 4, 2015 for U.S. Appl. No. 14/020,435.
Office Action dated Mar. 22, 2016 for U.S. Appl. No. 14/020,435.
Office Action dated Apr. 14, 2016 for U.S. Appl. No. 14/629,069.
Office Action dated Apr. 21, 2016 for U.S. Appl. No. 14/446,080.
Office Action dated May 5, 2016 for U.S. Appl. No. 14/214,774.
Office Action dated Jul. 22, 2016 for U.S. Appl. No. 14/214,771.
Office Action dated Jul. 30, 2015 for U.S. Appl. No. 14/446,080.
Office Action dated Aug. 15, 2016 for U.S. Appl. No. 14/447,099.
Office Action dated Sep. 21, 2015 for U.S. Appl. No. 14/629,069.
Office Action dated Sep. 22, 2016 for U.S. Appl. No. 14/020,435.
RAM Scientific. Safe-T-Fill Capillary Blood Collection Tubes. 2006.
Sarstedt. comprehensive catalogue. Cover page and pp. 1-43. last modified 2007.
International Search Report dated Dec. 18, 2016 for PCT/US2016/043435.
Notice of Allowance dated Jan. 27, 2017 for U.S. Appl. No. 13/214,774.
Notice of Allowance dated Feb. 17, 2017 for U.S. Appl. No. 14/020,435.
Office Action dated Dec. 29, 2016 for U.S. Appl. No. 14/446,080.
International Search Report dated Dec. 22, 2016 for PCT/US2016/051158.
Office Action dated Mar. 8, 2017 for U.S. Appl. No. 14/737,412.
Centers for Disease Control and Prevention. "Capillary Blood Sampling Protocol" 1997.
Deschka. "Blood Collection in Practice. A guideline for phlebotomists", Sep. 2009.
Home Blood Tests UK. "Home blood test kits. Collect at home, send to our laboratory." dated Jun. 13, 2012.
International Report and Written Opinion dated Nov. 20, 2014 for PCT/US2014/030070.
International Search Report and Written Opinion dated Aug. 28, 2014 for Application No. PCT/US2014/030792.

(56) References Cited

OTHER PUBLICATIONS

Massachusetts Department of Public Health. "Instructions for fingerstick sample collection for lead testing", Sep. 2012.
Medichecks. "Collection of a finger prick blood sample", Sep. 2012.
Office Action dated Oct. 14, 2014 for U.S. Appl. No. 14/447,099.
Office Action dated Nov. 28, 2014 for U.S. Appl. No. 14/320,471.
Office Action dated Mar. 20, 2015 for U.S. Appl. No. 14/320,471.
Office Action dated Mar. 25, 2015 for U.S. Appl. No. 14/447,099.
Office Action dated Apr. 6, 2015 for U.S. Appl. No. 14/446,080.
Office Action dated Jun. 16, 2015 for U.S. Appl. No. 14/020,435.
Office Action dated Aug. 5, 2015 for U.S. Appl. No. 14/098,177.
SARSTEDT. comprehensive catalogue. last modified 2007.
The International Search Report and the Written Opinion dated Feb. 13, 2014 for Application No. PCT/US2013/058627.
The International Search Report and the Written Opinion dated Jun. 10, 2014 for Application No. PCT/US13/00268.
U.S. Appl. No. 61/697,797, filed Sep. 6, 2012.
U.S. Appl. No. 61/733,886, filed Dec. 5, 2012.
U.S. Appl. No. 61/786,351, filed Mar. 15, 2013.
U.S. Appl. No. 61/798,873, filed Mar. 15, 2013.
U.S. Appl. No. 61/852,489, filed Mar. 15, 2013.
U.S. Appl. No. 61/875,030, filed Sep. 7, 2013.
U.S. Appl. No. 61/948,542, filed Mar. 5, 2014.
U.S. Appl. No. 61/952,112, filed Mar. 12, 2014.
U.S. Appl. No. 61/952,125, filed Mar. 12, 2014.
U.S. Appl. No. 61/952,130, filed Mar. 12, 2014.
U.S. Appl. No. 62/011,023, filed Jun. 11, 2014.
International Search Report and Written Opinion dated Sep. 25, 2014 for PCT/US2014/032092.
Notice of Allowance dated Oct. 17, 2017 for U.S. Appl. No. 14/629,069.
Notice of Allowance dated Nov. 3, 2017 for U.S. Appl. No. 14/737,412.
Office Action dated Dec. 28, 2017 for U.S. Appl. No. 14/855,249.
Office Action dated Feb. 12, 2018 for U.S. Appl. No. 14/447,099.
Office Action dated Apr. 21, 2017 for U.S. Appl. No. 14/855,249.
Office Action dated Aug. 25, 2016 for U.S. Appl. No. 14/855,249.

* cited by examiner

SYSTEMS, DEVICES, AND METHODS FOR BODILY FLUID SAMPLE TRANSPORT

CROSS-REFERENCE TO RELATED APPLICATIONS

This application claims priority to U.S. Provisional Application Ser. No. 61/733,886 entitled "Systems, Devices, and Methods for Bodily Fluid Sample Transport" and filed Dec. 5, 2012.

BACKGROUND

A blood sample for use in laboratory testing is typically obtained by venipuncture, which extracts blood from a subject's vein into one or more sealed vials or tubes. Unfortunately, currently available testing techniques often require a rather substantial volume of blood, sometimes extracting multiple vials of blood from each subject.

Because of the blood volume associated with traditional testing paradigm, the cost and logistics of transporting samples from a collection site to an analysis site can be substantial. The blood volume used for traditional testing also puts additional requirements on cooling the samples during transport so that sample integrity is not impacted due to thermally induced sample degradation. The traditional testing paradigm further requires that collection sites be staffed with skilled technicians that can reliably perform a venipuncture on a subject. Because of the high costs associated with the traditional paradigm of blood sample collection and testing, conventional laboratory testing is often not cost efficient, only available at select test locations, and unable to unburden itself from the substantial sunk costs of existing testing infrastructure.

SUMMARY

At least some of disadvantages associated with the prior art are overcome by at least some of the embodiments described in this disclosure.

In at least one embodiment described herein, methods are provided for the physical transport of small volumes of bodily fluid in liquid form from one location to another location. By way of nonlimiting example, the samples are collected in liquid form at a collection site, transported in liquid form, and arrive at an analysis site in liquid form. In many embodiments, the liquid form during transport is not held in a porous matrix, wicking material, webbing, or similar material that would prevent sample from being extracted in liquid form at the destination site. In one embodiment, small volume of sample in each sample vessel is in the range of about 1 ml to about 500 microliters. Optionally, small volumes are in the range of about 500 microliters to about 250 microliters. Optionally, small volumes are in the range of about 250 microliters to about 100 microliters. Optionally, small volumes are in the range of about 100 microliters to about 50 microliters. Optionally, small volumes are in the range of about 80 microliters to about 40 microliters. Optionally, small volumes are in the range of about 40 microliters to about 1 microliter. Optionally, small volumes are in the range of about 1 microliter to about 0.3 microliters. Optionally, small volumes are in the range of about 0.3 microliters or less.

In another embodiment described herein, the transport container may provide a high density of sample vessels per unit area held in a fixed manner during transport, but removable at the destination location. In one non-limiting example, the sample vessels are positioned in an array where there are at least six sample vessels per square inch, when viewing the array from top down. Optionally, there are at least eight sample vessels per square inch, when viewing the array from top down. Optionally, there are at least ten sample vessels per square inch, when viewing the array from top down. Any traditional techniques that ship multiple samples typically use large bags where the sample vessels therein are in a loose, unconstrained manner. In some embodiments, the transport container can hold certain sample vessels such as those from the same subject, closer together relative to horizontal or other spacing to adjacent sample vessels so that they can be visually identified as being from a common subject. Optionally, the transport container has openings to receive carriers that hold one or more sample vessels together, wherein those vessels have a common denominator such as but not limited to being from the same subject.

In embodiments, the sample vessels are adapted to aid in maintaining the samples in liquid form. In embodiments, the sample is treated prior to its arrival in a sample vessel in a manner adapted to maintain the sample in liquid form. For example, a sample vessel may include an anti-coagulating agent, or a sample may be treated with an anti-coagulating agent prior to, or during, transport to or into a sample vessel. In embodiments, an anti-coagulating agent may be selected from the group consisting of heparin, ethylenediaminetetraacetic acid, 4-hydroxycoumarins, vitamin K antagonist (VKA) anticoagulant, an anti-coagulant, or other additive.

In addition to the high density per unit area, some embodiments of the transport container also contain a high diversity of samples, including those that contain samples from a plurality of different subjects. By way of non-limiting example, the transport container may have four samples from one subject, two samples from another subject, and so-on until the majority or all of the available openings in the transport container are filled.

It should be understood that each of the samples can be destined for individually selected analysis and at least in one embodiment, are not grouped in the transport container based on tests to be performed. By way of non-limiting example, not all of the samples in the transport container are collected for the same test. A traditional test system may only group together for transport those samples destined for the exact same test. In at least one of the embodiments herein, there is a diversity of samples, each designated to receive its own set of tests. In such an embodiment, grouping in the transport container is not restricted to only those samples targeted for the same test. This can further simplify sample processing because sample transport does not need to be further segregated based on tests to be performed. Some embodiments of the transport container contain samples from at least three or more different patients. Some embodiments of the transport container contain samples from at least five or more different patients. Some embodiments of the transport container contain samples from at least ten or more different patients. Some embodiments of the transport container contain samples from at least twenty or more different patients.

By way of non-limiting example, one embodiment described herein may optionally use tray(s) that have slots for holding the sample vessels and/or sample vessel holders. In one embodiment, the tray may also double as a holding device during storage in a cooling chamber while awaiting more samples or transport. In one embodiment, the tray can itself also be cleaned and sterilized, because in some embodiments, the tray is removable from the transport container. In some embodiments, the tray in the container may be held in manner parallel to a cover of the container. Optionally, the tray may be held inside the container at an angle to the cover of the container. Optionally, the tray is irremovably fixed to the container. Optionally, the tray is integrally formed with the container itself. Optionally, multiple trays of same or different size or configuration may be placed inside the container.

In yet another embodiment described herein, methods are provided for shipping small volume sample vessels using a transport container with integrated thermal control unit and/or material that provides active and/or passive cooling. In one embodiment, the thermal control material may be but is not limited to embedded phase change material (PCM) material that maintains the temperature at a prior, or desired temperature. By way of non-limiting example, the phase change material can oppose changes in temperature around the critical temperature where the material would undergo a phase change. If the PCM is embedded, the container and the passive cooling element may be one and the same. Optionally, the transport container may use an active cooling system. Optionally, the transport container may use an active cooling system to keep and/or extend cooling time associated with a passive cooling component.

Optionally, the method comprises a single step for transferring multiple sample vessels from different subjects from a controlled temperature storage area into a transport container. By way of non-limiting example, this single step can transfer twenty-four or more sample vessels at one time from a storage location into a fixed position in the transport container. Optionally, this single step can transfer thirty-six or more sample vessels at one time from a storage location into a fixed position in the transport container. Optionally, this single step can transfer forty-eight or more sample vessels at one time from a storage location into a fixed position in the transport container. In such embodiments, the tray may be initially in a controlled thermal environment such as but not limited to a refrigerator wherein samples from various subjects are collected over time until a desired number is reached. In one such embodiment, the tray holding the sample vessel(s) in the transport container is the same tray holding the sample vessels in the storage area. Optionally, the tray may be the same as the storage holder that is used to hold samples prior to loading into the transport container. Because the same tray which holds the sample vessels will be used in the transport container, there is reduced risk that samples will be lost during this transfer, left out in a non-regulated thermal environment, or the like. Because substantially all sample vessels in the tray are accumulated in the controlled thermal storage area and then transferred in a single step, the samples all experience substantially the same thermal exposure while being transferred from the control thermal storage area into the transport container. Because sample vessels experience substantially the same exposure, there is less variability sample-to-sample due to different exposure times.

Optionally, the method comprises using an individually addressable sample vessel configuration. Optionally, groups of sample vessels such as those in a common carrier may be addressed in the pre-defined groups. Optionally, even sample vessels in a common carrier may be individually addressed. Although not a requirement for all embodiments herein, this can be of particular use when loading and/or unloading samples, sample vessels, and/or sample holders from the tray.

Some embodiments may use yet another container outside the transport container to provide further physical protection and/or thermal control capability. One or more of the transport container can be placed inside the outerbox and the combination is shipped from one location to a destination location. By way of non-limiting example, this can be in the form of a corrugated plastic outerbox, where the outerbox is configured to at least partially encase or enclose a transport container. In embodiments, an outerbox provides thermal insulation for a transport container enclosed therein. Some embodiments may use closed-cell extruded polystyrene foam outerbox. Some embodiments of the outerbox may be formed from thermoformed panels. Some embodiments of the outerbox may have its own active and/or passive thermal control unit. In embodiments, an outerbox provides cooling and thermal insulation for one or more transport containers enclosed therein. One or more embodiments of the outerbox may be configured to house one or more transport containers. Optionally, this container can also provide additional thermal control to the transport container by providing a thermally regulated environment between a desired temperature range to the transport container(s) therein. Optionally, this temperature range is between about 1 to 10 C, optionally 2 to 8 C, or between 2 to 6 C.

In yet another embodiment described herein, a method is provided for thermally characterizing the transport container after a number of cooling cycles. By way of non-limiting example, after certain number of cycles, the transport container may be thermally characterized to ensure that the container is continuing to perform within a desired range.

Some embodiments of the container and/or tray may include a thermal change indicator. In one non-limiting example, the indicator is integrated on a visible surface of the transport container, tray, and/or on the outerbox. In one non-limiting example, thermochromic ink may be used as an indicator of thermal change, particularly if the thermal change resulted in temperatures outside a desired range. In one embodiment, this indicator may be configured to have the entire box and/or tray change color. The change can be reversible or irreversible. Optionally, the indicator is positioned to be on only select portions of the transport container and/or tray, not the entire container or tray.

In one embodiment described herein, a method is provided comprising collecting a bodily fluid sample on a surface of a subject, wherein collected sample is stored in one or more sample vessels; providing a transport container to house at least two or more sample vessels in a first orientation; and arranging to have the sample vessels shipped in the transport container from a first location to a second location, wherein each of the sample vessels arrives at the second location holding a majority of its bodily fluid sample in a non-wicked, non-matrixed form that is removable from the sample vessels in liquid form and wherein the amount of sample in each of the sample vessels does not exceed about 2 ml.

In another embodiment described herein, a method is provided for shipping a plurality of sample vessels, the method comprising: providing a container configured to house at least five or more sample vessels each containing capillary blood; and arranging to have the sample vessels shipped in the container from a first location to a second location, wherein each of the sample vessels arrives holding a majority of its capillary blood in a liquid, non-wicked form that is removable from the sample vessels for further processing, and wherein the amount of capillary blood in each of the sample vessels does not exceed about 2 ml.

In another embodiment described herein, a method is provided for shipping a plurality of sample vessels for containing biological sample, the method comprising: providing a container configured to house at least five or more of the sample vessels, wherein the amount of sample in each of the sample vessels does not exceed about 2 ml; and shipping the container and sample vessels from a first location to a second location, wherein each of the sample vessels arrives holding a majority of its biological in a liquid, non-wicked form that is removable from the sample vessels for further processing.

In another embodiment described herein, a method is provided for shipping a plurality of sample vessels containing capillary blood, the method comprising: providing a container having a thermally-regulated interior region that is configured to house at least five or more sample vessels in a controlled configuration such that at least one cooling surface of the container is directed towards the sample vessels and transmits a controlled release of thermal cooling in accordance with a temperature profile that maintains the interior region between about 1 to 10 C during transport and without freezing the blood samples; and shipping the container from a first location to a second location, wherein each of the sample vessels arrives holding a majority of its capillary blood in a liquid, non-wicked form that is removable from the sample vessels for further processing.

In another embodiment described herein, a method is provided for shipping a plurality of blood sample vessels, the method comprising shipping a container having a thermally-controlled interior that is configured to house 10 or more sample vessels in an array configuration, wherein each of the vessels holds a majority of its blood sample in a free-flowing, non-wicked form and wherein there is about 1 ml or less of blood in each of the vessels and each of the vessels has an interior with at least a partial vacuum atmosphere; wherein sample vessels are held in the array configuration to position said sample vessels at controlled distance and orientation from a cooling surface, wherein there is at least one preferential thermal pathway from the surface to the sample vessel.

In another embodiment described herein, a method is provided for shipping a plurality of sub-1 ml sample vessels, the method comprising mixing sample with anti-coagulant prior to transferring sample into each of the sample vessels; associating each of the sample vessels with a subject and a panel of requested sample tests; and shipping a thermally-controlled container that houses the plurality of sub-1 ml sample vessels in an array configuration, wherein each of the vessels holds a majority of its sample in a free-flowing, non-wicked form, wherein vessels are arranged such that there are at least two vessels in each container is associated with each subject, wherein at least a first sample includes a first anticoagulant and a second sample includes a second anticoagulant in the matrix.

In another embodiment described herein, a method is provided comprising a) placing said plurality of sample vessels in a temperature controlled sample vessel comprising a controlled uniform thermal profile, high heat of fusion material configured to be in thermal communication with the sample vessels, wherein the material does not cause freezing of sample fluid in the sample vessels; b) placing said thermal profile sample vessel in a product cavity defined by at least top and bottom walls of a transport container; c) placing an active cooling device in thermal communication with said cavity whereby said cooling device is adapted to cool said cavity upon activation, said sorption cooling device comprising an absorber positioned so as to dissipate heat generated in said absorber outside of said product cavity; d) activating said cooling device to initiate cooling of said cavity; e) transporting said transport container from a first location to a second location; and f) removing said product from said cavity.

In another embodiment described herein, a method of shipping a plurality of sub-1 ml sample vessels is provided comprising: shipping a thermally-controlled container that houses the plurality of sub-1 ml sample vessels in an array configuration, wherein each of the vessels holds a majority of its sample in a free-flowing, non-wicked form and wherein vessels are arranged such that there are at least two vessels in each container is associated with each subject, wherein at least a first sample includes a first anticoagulant and a second sample includes a second anticoagulant in the matrix.

It should be understood that any of the embodiments herein can be adapted to have one or more of the following features. In one non-limiting example, the bodily fluid sample is blood. Optionally, the bodily fluid sample is capillary blood. Optionally, collecting the bodily fluid sample comprises making at least one puncture on the subject to release the bodily fluid, wherein the puncture is not a venipuncture. Optionally, collecting comprises using at least one microneedle to make at least one puncture on the subject. Optionally, collecting comprises using at least one lancet to make at least one puncture on the subject. Optionally, the puncture is formed by finger prick. Optionally, the puncture is formed by pricking skin on a forearm of the subject. Optionally, the puncture is formed by pricking skin on a limb of the subject. Optionally, the surface is the skin of the subject. Optionally, the sample vessel has an interior that is initially at sub-atmospheric pressure. Optionally, the sub-atmospheric pressure is at least a partial vacuum. Optionally, the interior of the sample vessel is at a sub-atmospheric pressure that is at least at a pressure below ambient pressure. Optionally, the sub-atmospheric pressure is selected to provide sufficient force to draw a desired volume of sample into the sample vessel. Optionally, the transport container contains at least five or more sample vessels. Optionally, the transport container ships bodily fluid samples from a plurality of different subjects. Optionally, information associated with each of the sample vessels determine what tests will be run on the bodily fluid sample therein. Optionally, the transport container is placed inside another container during shipping. Optionally, the method further comprises pre-processing sample in the sample vessels prior to shipping to the second location.

Optionally, the container has a sample vessel array density of at least about 4 vessels per square inch. Optionally, a cooling surface in the transport container provides a temperature profile within a desired range for sample vessels in the container. Optionally, the sample vessels are individually addressable. Optionally, the method further comprises using a cooled tray to hold the samples vessels in a cooling chamber prior to loading the vessels into the container and the same tray is used to hold the sample vessels in the container, wherein the samples are placed into container with the cooled tray. Optionally, sample vessels are arranged such that there are at least two vessels in each container with bodily sample fluid from the same subject, wherein at least a first sample includes a first anticoagulant and a second sample includes a second anticoagulant in the matrix. Optionally, the fluid sample comprises capillary blood for use in CLIA compliant laboratory testing. Optionally, the fluid sample comprises blood for use in CLIA compliant laboratory testing. Optionally, a housing providing a controlled thermal profile and high heat of fusion material providing at least one cooling surface facing the containers.

Optionally, a high heat of fusion material is embedded in material used to form the container. Optionally, a controlled thermal profile, high heat of fusion material comprises about 30% to 50%. Optionally, a controlled thermal profile, high heat of fusion material comprises about 10% to 30%. Optionally, the method further comprises a housing of metallic material having a resting temperature less than ambient temperature.

Optionally, the method further comprises scanning an information storage unit on each sample at the receiving site and automatically placing the container into a cartridge. Optionally, the method further comprises scanning an information storage unit on each sample at the receiving site and automatically placing the container into a cartridge. Optionally, the method further comprises using the same tray to hold sample vessels in the array configuration when in a refrigeration device prior to transport and in the transport container during transport. Optionally, the method further comprises using a tray for holding the sample vessels that comprises a highly thermally conductive material. Optionally, the tray comprises a plurality of slots having a shape to hold sample vessels holders in a preferential orientation. Optionally, the tray is configured to directly engage sample vessel holders. Optionally, a tray locking mechanism is used to hold the tray within the container, wherein the tray locking mechanism releases the tray only upon application of magnetic force. Optionally, the method comprises maintaining a temperature range in the 2 to 8 C during transport. Optionally, the method further comprises a temperature control material that maintains above freezing but about 10 C or less during transport. Optionally, the method comprises using a temperature threshold detector to indicate if the sample vessel reaches a temperature outside a threshold level. Optionally, the method further comprises scanning a vessel in the tray prior to shipping to determine if a processing step on the sample had not been performed; using a processor to perform or re-perform a step. Optionally, the method further comprises a single-step loading of the sample vessel into the tray and then a single-step loading of the tray into the transport container.

Optionally, the transport container has a first surface configured to define a thermally conductive pathway to the controlled thermal profile, high heat of fusion material in the container. Optionally, the first surface is configured to be in direct contact with another surface cooled by a sorption cooling device. Optionally, the method comprises simultaneous bar code scanning of sample vessels in the tray. Optionally, the method comprises simultaneous bar code scanning undersides of sample vessels in the tray. Optionally, the method comprises bar code scanning rows of sample vessels. Optionally, the method comprises bar code scanning undersides of rows of sample vessels. Optionally, the method comprises shipping a plurality of the sample vessels in an inverted orientation. Optionally, the method comprises shipping a plurality of the sample vessels wherein blood cells and plasma are separated by a barrier material in the sample vessels. Optionally, the method comprises opening the container by unlocking it and opening it, wherein at least one hinge holds two pieces together. Optionally, the tray has at least one magnetic contact point for removing the tray from the container. Optionally, a computer controlled end effector is used to load and/or unload sample vessels from the transport container, wherein before, during, or after unloading, a reader obtains information from at least one information storage unit attached to one or more sample vessels.

In yet another embodiment herein, a thermal-controlled transport container is provided for use in shipping a plurality of sample vessels, the transport container comprising: a container having at least a top, bottom, and side walls together defining a cavity, wherein at least one of said top, bottom and side walls comprises a phase change material; a frame sized to fit within the cavity and defining openings configured for holding a plurality of sample vessels and having sidewalls configured to be in contact with sidewalls of the sample vessels, wherein containers are arranged such that each patient has at least a first sample with a first anticoagulant and a second sample with a second anticoagulant in the matrix.

In another embodiment described herein, a thermal-controlled transport container is provided for use in shipping a plurality of sample vessels, the transport container comprising: a) a bottom container portion comprising a bottom wall and at least a first sidewall defining a cavity adapted to contain a product therein; b) a top container portion comprising a top surface and a bottom surface and adapted to combine with said bottom container portion to define a product cavity, said top container portion forming a top wall for said container; wherein at least one of said top, bottom and side walls comprises a phase change material.

In another embodiment described herein, a thermal-controlled transport container is provided for use in shipping a plurality of sample vessels, the transport container comprising: a) a bottom container portion comprising a bottom wall and at least a first sidewall defining a cavity adapted to contain a product therein; b) a top container portion comprising a top surface and a bottom surface and adapted to combine with said bottom container portion to define a product cavity, said top container portion forming a top wall for said container; c) a holder for defining a plurality of sample vessel holding spaces to position the sample vessels in a pre-determined orientation; wherein at least one of said top, bottom and side walls comprises a phase change material.

In another embodiment described herein, a container is provided for shipping sample vessels, the container comprising: a generally rectangular floor; generally parallel sides projecting from longitudinal edges of the floor; generally parallel ends projecting from end edges of the floor and bridging the sides; a cover fittable over the sides and ends and forming therewith and with the floor a generally closed space; a sample vessel holder removably coupled to the floor in an interior of the container and configured to define vessel-holding spaces. Optionally, the vessel holding spaces are configured to hold air-evacuated blood collection tubes having an interior volume of about 2 ml or less.

In another embodiment described herein, a thermal-controlled transport container is provided for use in shipping a plurality of sample vessels, the transport container comprising: means for holding a plurality of sample vessels in at least one fixed orientation; means for thermally controlling temperature of the sample vessels to be within a desired range of about 0 to 10 C; wherein the means from holding the plurality of sample vessels is removable from the transport container. Optionally, the vessel holding spaces are configured to hold air-evacuated blood collection tubes having an interior volume of about 2 ml or less.

It should be understood that some embodiments may comprise a kit that includes a transport container as recited in any of the above. Optionally, the kit includes a transport container and instructions for their use.

In one embodiment described herein, a method is described for providing a whole blood sample and/or partition thereof from a sender to a recipient. The method comprises transporting a package comprising a sample vessel comprising one or more channels that contains (a) a whole blood sample and/or partition thereof in fluid state having a volume less than or equal to about 200 microliters (ul) and (b) one or more reagents used for preserving one or more analytes in the whole blood sample and/or partition thereof for analysis until at least when whole blood sample and/or partition thereof reaches the recipient, and wherein the depositing results in delivery of the sample vessel to the recipient. By way of non-limiting example, transporting the sample vessel may occur by using a parcel delivery service, a courier, or other shipping service.

In one embodiment described herein, a method is described for preparing a whole blood sample for delivery to a sample processing station. The method comprises depositing a sample vessel having a whole blood sample in fluid state and a volume less than or equal to about 200 ul with a delivery service for delivering the sample vessel to the sample processing location for processing the whole blood sample. The sample vessel may be prepared by (a) drawing the whole blood sample from a subject with the aid of a capillary channel and (b) placing the whole blood sample into the sample vessel, wherein the whole blood sample is preserved in fluid state with one or more reagents contained in the capillary channel and/or the sample vessel.

It should be understood that any of the embodiments herein may be adapted to have one or more of the following features. By way of non-limiting example, the sample in some embodiments may be a semi-solid or gel state. This may occur after the sample is in the sample vessel. Optionally, the delivery service is a mail delivery service. Optionally, the blood sample is collected from the subject at a point of care location. Optionally, the point of care location is a home of the subject. Optionally, the point of a care location is the location of a healthcare provider.

In another embodiment described herein, a method for processing a whole blood sample comprises receiving at a processing station from a parcel delivery service, a sample vessel having a whole blood sample less than or equal to about 200 ul, wherein the sample vessel is received at the processing station with the whole blood sample in a fluid state; and performing, at the processing station, at least one pre-analytical and/or analytical assay on the whole blood sample in a fluid state.

It should be understood that any of the embodiments herein may be adapted to have one or more of the following features. By way of non-limiting example, the assay has one or more steps. Optionally, the sample vessel is included in a housing having one or more environmental control zones. Optionally, the housing is adapted to control a humidity of each of the environmental control zones. Optionally, the housing is adapted to control a pressure of each of the environmental control zones.

In yet another embodiment described herein, a computer-implemented method is provided for queuing a blood sample for processing at a processing location. The method comprises (a) identifying, with the aid of a geolocation system having a computer processor, the geolocation of a sample vessel having the blood sample; (b) estimating, with the aid of a computer processer, delivery time of the sample vessel to the processing location; and (c) based on the estimated time of delivery, providing a notification for preparative work for processing the sample at the processing location.

In yet another embodiment described herein, a method is described for preparing a whole blood sample for delivery to a sample processing station. The method comprises depositing a sample vessel having a whole blood sample in fluid state with a delivery service for delivering the sample vessel to the sample processing location for processing the whole blood sample, wherein the sample vessel is prepared by (a) drawing the whole blood sample from a subject using a device and (b) placing the whole blood sample into the sample vessel.

Optionally, depositing may encompass pick-up and/or drop-off. Optionally, processing may include pre-analytic, analytic and post-analytic processing. Optionally, delivery service may include a subject's delivery service or a third party delivery service. Optionally, the whole blood sample is preserved in fluid state with one or more reagents contained in the capillary channel or the sample vessel.

In yet another embodiment described herein, a method is provided for processing a whole blood sample at a processing station. The method comprises receiving, at the processing station from a delivery service, a sample vessel having a whole blood sample, wherein the sample vessel is prepared by (a) drawing the whole blood sample from a subject using a collection device and (b) placing the whole blood sample into the sample vessel. The method also includes performing, at the processing station, at least one pre-analytical or analytic assay on the whole blood sample.

It should be understood that any of the embodiments herein may be adapted to have one or more of the following features. By way of non-limiting example, with the aid of a computer processor, providing a time for completion of the processing from the estimated time of delivery. Optionally, the method includes queuing the sample vessel for processing upon estimating the time of delivery of the sample vessel at the processing location. Optionally, the geolocation of the sample vessel is identified with the aid of a communications network.

In one embodiment described herein, a computer-implemented method is described for providing an estimated time of completion for the processing of a blood sample. The method comprises receiving information about a sample vessel transported through a delivery service to a processing station that is for sample processing, the sample vessel having a blood sample removed from a subject. The method also includes calculating, with the aid of a computer processor, a position of the blood sample in a processing queue at the processing station, wherein the predicting is based on (i) information about the position of blood samples from other subjects in the processing queue and (ii) information about the geographic location of other sample vessels having blood samples from other subjects in relation to the sample vessel having the blood sample removed from the subject. The method includes predicting a time for processing the blood sample at the processing station upon delivery of the sample vessel by the delivery service to the processing station; and based on the predicting and an estimated time of delivery of the sample vessel to the processing station, providing the subject or a healthcare provider associated with the subject an estimated time for processing the blood sample from the subject, the estimated time measured from the point the sample vessel is deposited with the delivery service. Optionally, the sample is transported to a plurality of processing stations. It should be understood that processing as used herein is to be broadly interpreted and may include pre-analytical, analytical, and/or post-analytical step(s).

In yet another embodiment described herein, a computer-implemented method is described for providing an estimated time of completion for the processing of a blood sample from a subject. The method comprises receiving information about a sample vessel transported through a delivery service to a processing station that is for sample processing, the sample vessel having a blood sample removed from the subject. The method also includes calculating, with the aid of a computer processor, a position of the blood sample in a processing queue at the processing station, wherein the predicting is based on (i) information about the position of blood samples from other subjects in the processing queue and (ii) information about the geographic location of other sample vessels having blood samples from other subjects in relation to the sample vessel having the blood sample removed from the subject. The method includes predicting a time for processing the blood sample at the processing station upon delivery of the sample vessel by the delivery service to the processing station; and based on the predicting and an estimated time of delivery of the sample vessel to the processing station, allocating one or more resources at the processing station for processing the blood sample upon delivery to the processing station.

It should be understood that any of the embodiments herein may be adapted to have one or more of the following features. By way of non-limiting example, the sample vessel has an information storage unit that allows identification of the sample vessel by the delivery service and/or the processing location. Optionally, the information storage unit is a radiofrequency identification (RFID) tag. Optionally, the information storage unit is a barcode. Optionally, the information storage unit is a microchip. Optionally, the sample vessel comprises one or more sensors for collecting one or more of the temperature of the blood sample, the pressure of the sample vessel, the pH of the blood sample, the turbidity of the blood sample, the viscosity of the blood sample. Optionally, the processing location processes collected blood samples on an on-demand basis. Optionally, the sample vessel includes a geo-location device for providing the location of the sample vessel. Optionally, the anticoagulating agent is selected from the group consisting of heparin, ethylenediaminetetraacetic acid, an anti-coagulant, or other additive. Optionally, the container, wherein the vessel holding spaces is configured to hold air-evacuated blood collection tubes, are configured to hold air-evacuated blood collection tubes having a partial vacuum of at most about 60% vacuum This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference. References cited herein are hereby incorporated by reference in their entirety, except to the extent that they conflict with teachings explicitly set forth in this specification.

BRIEF DESCRIPTION OF THE DRAWINGS

FIGS. 2A-3 show various views of a thermally controlled sample vessel transport device according to at least one embodiment described herein.

DESCRIPTION OF THE SPECIFIC EMBODIMENTS

Figures 1A, 1B:
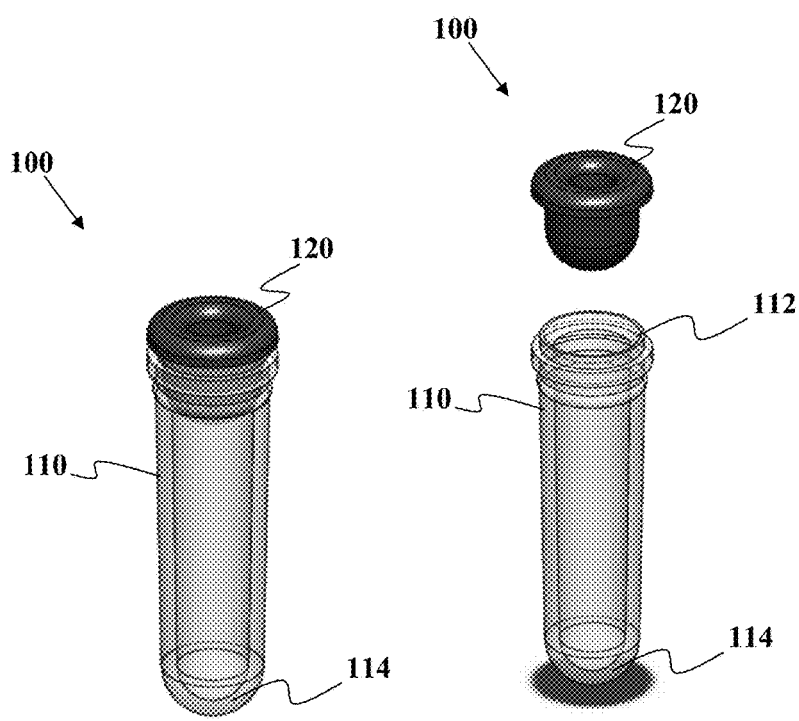
FIGS. 1A-1G show various views of sample vessels according to embodiments described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural references unless the context clearly dictates otherwise. Thus, for example, reference to "a material" may include mixtures of materials, reference to "a compound" may include multiple compounds, and the like.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

As used herein, "a bodily fluid sample collector" or any other collection mechanism can be disposable. For example, a bodily fluid collector can be used once and disposed. A bodily fluid collector can have one or more disposable components. Alternatively, a bodily fluid collector can be reusable. The bodily fluid collector can be reused any number of times. In some instances, the bodily fluid collector can include both reusable and disposable components.

As used herein, "a sample collection unit" and/or any other portion of the device may be capable of receiving a single type of sample, or multiple types of samples. For example, the sample collection unit may be capable of receiving two different types of bodily fluids (e.g., blood, tears). In another example, the sample collection unit may be capable of receiving two different types of biological samples (e.g., urine sample, stool sample). Multiple types of samples may or may not be fluids, solids, and/or semi-solids. For example, the sample collection unit may be capable of accepting one or more of, two or more of, or three or more of a bodily fluid, secretion and/or tissue sample.

As used herein, "non-wicked, non-matrixed form" means that a liquid or suspension is not absorbed by or pulled into a webbing, mesh, fiber pad, absorbent material, absorbent structure, percolating network of fibers, or the like which alters the form of the liquid or suspension or traps components of the sample therein to an extent that the integrity of sample in liquid form is changed and the sample cannot be extracted in liquid form while still maintaining sample integrity for sample analysis.

Sample Vessels

FIGS. 1A-1B show one nonlimiting example of a sample vessel 100 that may be utilized with a sample collection device in accordance with an embodiment described herein. In some instances, the sample vessels may be supported by the sample collection device. Optionally, the sample vessels may be encompassed or surrounded by a portion of the sample collection device. In one example, the sample collection device may have a first configuration where the sample vessels are completely enclosed. A second configuration may be provided where the sample collection device may be opened and at least a portion of the sample vessels may be exposed. In some examples, the sample vessels may be supported and/or at least partially enclosed by a holder of the sample collection device. The holder may be separable from the rest of the sample collection device, thereby providing access to the sample vessels therein.

In the case of bodily fluid collection, the sample fluid may be extracted from the patient using a sample collection device such as but not limited to that described in U.S. Patent Application Ser. No. 61/697,797 filed Sep. 6, 2012 and fully incorporated herein by reference. In the non-limiting example of blood samples, some embodiments may collect the blood sample through collection of capillary blood from the subject. This may occur by way of a wound, a penetration site, or other access site to capillary blood from the subject. Optionally, blood could also be collected by venipuncture or other puncture of a blood vessel to obtain blood sample for loading into the sample vessel(s). Other types of devices and techniques used to collect bodily fluid are not excluded.

A bodily fluid may be drawn from a subject and provided to a device in a variety of ways, including but not limited to, fingerstick, lancing, injection, pumping, swabbing, pipetting, venous draw, venapuncture, and/or any other technique described elsewhere herein. In some embodiments, the sample may be collected from the subject's breath. The bodily fluid may be provided using a bodily fluid collector. A bodily fluid collector may include a lancet, capillary, tube, pipette, syringe, needle, microneedle, pump, or any other collector described elsewhere herein. In some embodiments, the sample may be a tissue sample which may be provided from the subject. The sample may be removed from the subject or may have been cast off by the subject.

In one embodiment, a lancet punctures the skin of a subject and withdraws a sample using, for example, gravity, capillary action, aspiration, pressure differential or vacuum force. The lancet, or any other bodily fluid collector, may be part of the device, part of a cartridge of the device, part of a system, or a standalone component. Where needed, the lancet or any other bodily fluid collector may be activated by a variety of mechanical, electrical, electromechanical, or any other known activation mechanism or any combination of such methods.

In one example, a subject's finger (or other portion of the subject's body) may be punctured to yield a bodily fluid. The bodily fluid may be collected using a capillary tube, pipette, swab, drop, or any other mechanism known in the art. The capillary tube or pipette may be separate from the device and/or a cartridge of the device that may be inserted within or attached to a device, or may be a part of a device and/or cartridge. In another embodiment where no active mechanism is required, a subject can simply provide a bodily fluid to the device and/or cartridge, as for example, with a saliva sample.

A bodily fluid may be drawn from a subject and provided to a device in a variety of ways, including but not limited to, fingerstick, lancing, injection, and/or pipetting. The bodily fluid may be collected using venous or non-venous methods. The bodily fluid may be provided using a bodily fluid collector. A bodily fluid collector may include a lancet, capillary, tube, pipette, syringe, venous draw, or any other collector described elsewhere herein. In one embodiment, a lancet punctures the skin and withdraws a sample using, for example, gravity, capillary action, aspiration, or vacuum force. The lancet may be part of the device, part of the cartridge of the device, part of a system, or a standalone component. Where needed, the lancet may be activated by a variety of mechanical, electrical, electromechanical, or any other known activation mechanism or any combination of such methods. In one example, a subject's finger (or other portion of the subject's body) may be punctured to yield a bodily fluid. Examples of other portions of the subject's body may include, but are not limited to, the subject's hand, wrist, arm, torso, leg, foot, or neck. The bodily fluid may be collected using a capillary tube, pipette, or any other mechanism known in the art. The capillary tube or pipette may be separate from the device and/or cartridge, or may be a part of a device and/or cartridge. In another embodiment where no active mechanism is required, a subject can simply provide a bodily fluid to the device and/or cartridge, as for example, could occur with a saliva sample. The collected fluid can be placed within the device. A bodily fluid collector may be attached to the device, removably attachable to the device, or may be provided separately from the device.

Sample obtained from a subject may be stored in a sample vessel 100. In one embodiment described herein, the sample vessel 100 comprises a body 110 and a cap 120. In some instances, at least portions of the sample vessel body may be formed from a transparent or translucent material. The sample vessel body may permit a sample provided within the sample vessel body to be visible when viewed from outside the sample vessel. The sample vessel body may be optically transmissive. The sample vessel body may be formed of a material that may permit electromagnetic radiation to pass through. In some instances, the sample vessel body may be formed of a material that may permit selected wavelengths of electromagnetic radiation to pass through while not permitting other non-selected wavelengths of electromagnetic radiation to pass through. In some instances a portion or all of the body may be formed of a material that is opaque along selected wavelengths of electromagnetic radiation, such as wavelengths for visible light. Optionally, some portions of the sample vessel body may be shaped to provide a certain optical path length. Optionally, some portions of the sample vessel body may be shaped to provide a flat surface (exterior and/or interior) or other structure to allow for analysis of sample while it is in the sample vessel.

In one embodiment, an open end and a closed end may be provided on a sample vessel body 110. The open end may be a top end 112 of the sample vessel 100, which may be at the end which may be configured to engage with a cap. The closed end may be a bottom end 114 of the sample vessel, which may be at the end of the sample vessel opposite the cap. In alternative embodiments, a bottom end may also be an open end that may be closable with a floor. In some embodiments, the cross-sectional area and/or shape of the top end and the bottom end may be substantially the same. Alternatively, the cross-sectional area of the top end may be larger than the cross-sectional area of the bottom end, or vice versa. There may be variations and alternatives to the embodiments described herein and that no single embodiment should be construed to encompass the entire invention.

In one embodiment, a sample vessel body may have an interior surface and an exterior surface. The surfaces of the sample vessel body may be smooth, rough, textured, faceted, shiny, dull, contain grooves, contain ridges, or have any other feature. The surface of the sample vessel body may be treated to provide a desired optical property. The interior surfaces and exterior surfaces may have the same properties or may be different. For example, an exterior surface may be smooth while the interior surface is rough.

Optionally, the sample vessel body may have a tubular shape. In some instances, the sample vessel body may have a cylindrical portion. In some instances, the sample vessel may have a circular cross-sectional shape. Alternatively, the sample vessel may have any other cross-sectional shape which may include elliptical, triangular, quadrilateral (e.g., square, rectangular, trapezoidal, parallelogram), pentagonal, hexagonal, heptagonal, octagonal, or any other shape. The cross-sectional shape of the sample vessel may or may not have a convex and/or concave shape. The cross-sectional shape of the sample vessel may remain the same along the length of the sample vessel, or may vary. The sample vessel may have a prismatic shape along the length of the body. The prism may have a cross-sectional shape as those described herein.

Optionally, the bottom 114 of the sample vessel may be flat, tapered, rounded, or any combination thereof. In some instances, the sample vessel may have a hemispherical bottom. In other embodiments, the sample vessel may have a rounded bottom with a flat portion. The sample vessel may or may not be capable of standing on a flat surface on its own.

In one embodiment, the sample vessels 100 may be sized to contain a small fluid sample. In some embodiments, the sample vessels may be configured to contain no more than about 5 ml, 4 ml, 3 ml, 2 ml, 1.5 mL, 1 mL, 900 uL, 800 uL, 700 uL, 600 uL, 500 uL, 400 uL, 300 uL, 250 uL, 200 uL, 150 uL, 100 uL, 80 uL, 50 uL, 30 uL, 25 uL, 20 uL, 10 uL, 7 uL, 5 uL, 3 uL, 2 uL, 1 uL, 750 nL, 500 nL, 250 nL, 200 nL, 150 nL, 100 nL, 50 nL, 10 nL, 5 nL, 1 nL, 500 pL, 300 pL, 100 pL, 50 pL, 10 pL, 5 pL, or 1 pL. By way of non-limiting example, the sample vessels may have the information storage units thereon such as discussed for FIGS. 1F and 1G. In one non-limiting example, the sample vessels 100 may hold the small volume of sample fluid in liquid form without the use of a wicking material, mesh, solid matrix, or the like to hold the sample fluid during transport. This allows the sample fluid to be substantially removed in liquid form from the sample vessel without loss of sample or sample integrity due to liquid being absorbed by the wicking or other material.

Optionally, the sample vessels 100 may be configured to contain no more than several drops of blood, a drop of blood, or no more than a portion of a drop of blood. For example, the sample vessel may have an interior volume of no greater than the amount of fluid sample it is configured to contain. Having a small volume sample vessel may advantageously permit storage and/or transport of a large number of sample vessels within a small volume. This may reduce resources used to store and/or transport the sample vessels. For example, less storage space may be required. Additionally, less cost and/or fuel may be used to transport the sample vessels. For the same amount of exertion, a larger number of sample vessels may be transported.

In some embodiments, the sample vessel 100 may have a small length. For example, the sample vessel length may be no greater than 8 cm, 7 cm, 6 cm, 5 cm, 4 cm, 3.5 cm, 3 cm, 2.5 cm, 2 cm, 1.7 cm, 1.5 cm, 1.3 cm, 1.1 cm, 1 cm, 0.9 cm, 0.8 cm, 0.7 cm, 0.6 cm, 0.5 cm, 0.4 cm, 0.3 cm, 0.2 cm, 0.1 cm, 700 um, 500 m, 300 um, 100 um, 70 um, 50 um, 30 um, 10 um, 7 um, 5 um, 30 um, or 1 um. In some instances, the greatest dimension of the sample vessel (e.g., length, width, or diameter) may be no greater than 8 cm, 7 cm, 6 cm, 5 cm, 4 cm, 3.5 cm, 3 cm, 2.5 cm, 2 cm, 1.7 cm, 1.5 cm, 1.3 cm, 1.1 cm, 1 cm, 0.9 cm, 0.8 cm, 0.7 cm, 0.6 cm, 0.5 cm, 0.4 cm, 0.3 cm, 0.2 cm, 0.1 cm, 700 um, 500 m, 300 um, 100 um, 70 um, 50 um, 30 um, 10 um, 7 um, 5 um, 30 um, or 1 um.

The sample vessel 100 may have any cross-sectional area. The cross-sectional area may be no greater than about 16 $cm^2$, 8 $cm^2$, 7 $cm^2$, 6 $cm^2$, 5 $cm^2$, 4 $cm^2$, 3.5 $cm^2$, 3 $cm^2$, 2.5 $cm^2$, 2 $cm^2$, 1.5 $cm^2$, 1 $cm^2$, 0.9 $cm^2$, 0.8 $cm^2$, 0.7 $cm^2$, 0.6 $cm^2$, 0.5 $cm^2$, 0.4 $cm^2$, 0.3 $cm^2$, 0.2 $cm^2$, 0.1 $cm^2$, 0.07 $cm^2$, 0.05 $cm^2$, 0.03 $cm^2$, 0.02 $cm^2$, 0.01 $cm^2$, 0.5 $cm^2$, 0.3 $cm^2$, or 0.1 $cm^2$. The cross-sectional area may remain the same or may vary along the length of the sample vessel.

The sample vessel 100 may have any thickness. The thickness may remain the same along the length of the sample vessel or may vary. In some instances, the thickness may be selected and/or may vary in order to provide a desired optical property. In some instances, the thickness may be no greater than 5 mm, 3 mm, 2 mm, 1 mm, 700 um, 500 um, 300 um, 200 um, 150 um, 100 um, 70 um, 50 um, 30 um, 10 um, 7 um, 5 um, 3 um, 1 um, 700 nm, 500 nm, 300 nm or 100 nm.

In one embodiment, the sample vessel 100 may have a shape conducive to enabling centrifugation of small volume blood samples. This allows the collected sample in the sample vessels to be taken directly to a centrifuge without having to further transfer the sample fluid to yet another sample vessel that is used in the centrifuge device.

Optionally, the sample vessels may contain a cap 120. The cap 120 may be configured to fit over an open end of the sample vessel. The cap may block the open end of the sample vessel. The cap may fluidically seal the sample vessel. The cap may form a fluid-tight seal with the sample vessel body. For example, the cap may be gas and/or liquid impermeable. Alternatively, the cap may permit certain gases and/or liquids to pass through. In some instances, the cap may be gas permeable while being liquid impermeable. The cap may be impermeable to the sample. For example, the cap may be impermeable to whole blood, serum or plasma.

Optionally, the cap may be configured to engage with the sample vessel body in any manner. For example, the cap may be press-fit with the sample vessel body. A friction fit and/or interference fit may permit the cap to stay on the body. In other examples, a locking mechanism may be provided, such as a sliding mechanism, clamp, fastener, or other technique. In some instances, the cap and/or the sample vessel body may be threaded to permit a screw-type engagement. In other examples, adhesives, welding, soldering, or brazing may be utilized to connect the cap to the sample vessel body. The cap may be removably attached to the sample vessel body. Alternatively, the cap may be permanently affixed to the sample vessel body.

In some instances, a portion of the cap may fit into a portion of the sample vessel body. The cap may form a stopper with the sample vessel body. In some instances, a portion of the sample vessel body may fit into a portion of the cap. The plug may include a lip or shelf that may hang over a portion of the sample vessel body. The lip or shelf may prevent the cap from sliding into the sample vessel body. In some instances, a portion of a cap may overlie a top and/or side of the sample vessel body. Optionally, some embodiments may include an additional part in the vessel assembly such as cap holder. In one embodiment, the purpose of the cap holder is to maintain a tight seal between the cap and sample vessel. In one embodiment, the cap holder engages an attachment, lip, indentation, or other attachment location on the outside of the sample vessel to hold the cap in position. Optionally, some embodiments can combine the function of both the cap and the cap holder into one component.

In some embodiments, the sample vessel body may be formed of a rigid material. For example, the sample vessel body may be formed of a polymer, such as polypropylene, polystyrene, or acrylic. In alternate embodiments, the sample vessel body may be semi-rigid or flexible. The sample vessel body may be formed from a single integral piece. Alternatively, multiple pieces may be used. The multiple pieces may be formed from the same material or from different materials.

Optionally, the sample vessel cap may be formed of an elastomeric material, or any other material described elsewhere herein. In some instances, the cap may be formed from a rubber, polymer, or any other material that may be flexible and/or compressible. Alternatively, the cap may be semi-rigid or rigid. The sample vessel cap may be formed from a high friction material. The sample vessel cap may be capable of being friction-fit to engage with the sample vessel body. When the sample vessel cap is engaged with the sample vessel body, a fluid-tight seal may be formed. The interior of the sample vessel body may be fluidically isolated from the ambient air. In some instances, at least one of the cap and/or portion of the sample vessel body contacting the cap may be formed from a high friction and/or compressible material.

In one embodiment, the cap 120 may be a needle and/or a cannula-penetrable self-sealing gas-proof closure in sealing engagement in the open end of the sample vessel so as to maintain a vacuum and/or a close atmosphere inside the sample vessel. In some embodiments, the interior of the sample vessel is only at a partial vacuum and not at a full vacuum. Excessive vacuum can damage formed blood components in the sample fluid. By way of non-limiting example, the partial vacuum is in the range of about 50 to 60% of a full vacuum. Optionally, the partial vacuum does not exceed about 60% of a full vacuum. Optionally, the partial vacuum does not exceed about 50% of a full vacuum. Optionally, the partial vacuum does not exceed about 40% of a full vacuum. By way of non-limiting example, the partial vacuum is in the range of about 10% to about 90% of a full vacuum, or between about 20% to about 70%, or between about 30% to about 60% of a full vacuum. By way of non-limiting example, the partial vacuum is in the range of about 10% to about 60% of a full vacuum, or between about 20% to about 50%, or between about 30% to about 50% of a full vacuum. In this manner, a reduced amount of force is exerted on the bodily fluid sample to minimize issues with regards to sample integrity. Optionally, after sample transfer, the atmosphere is at ambient pressure. Optionally, after sample transfer, the atmosphere is at some partial vacuum. Optionally, only one of the plurality of sample vessels is at partial vacuum, while others are at higher vacuum levels or at full vacuum.

In some embodiments, the cap 120 may be a closure device having one end interior of the sample vessel and another end exterior of the sample vessel, wherein the end interior having a surface in continuous sealing contact with the sample vessel, the end interior having an annular sleeve extending from the surface toward the closed end, the annular sleeve having a first notch extending through a wall of the annular sleeve and juxtaposed against the sample vessel. In one embodiment, the closure has an indented ring formed about the first notch of the end interior and the indented ring engaging a hump of the tubular sample vessel.

Optionally, the sample vessel cap may be formed from a single integral piece. Alternatively, multiple pieces may be used. The multiple pieces may be formed from the same material or from different materials. The cap material may be the same as or different from the sample vessel body material. In one example, the sample vessel body may be formed from an optically transmissive material while the cap is formed from an opaque material.

Optionally, the cap 120 may be removably engaged with the body. A portion of the cap may be insertable into the body. The cap may include a lip which may rest on top of the body. The lip is not inserted into the body. In this non-limiting example, the lip may prevent the cap from being entirely inserted into the body. The lip may form a continuous flange around the cap. In some instances, a portion of the lip may overlap or overlie a portion of the body. A portion of the body may be insertable into a portion of the cap.

Optionally, the portion of the cap that may be insertable into the body may have a rounded bottom. Alternatively, the portion may be flat, tapered, curved, contoured, or have any other shape. The cap may be shaped to be easily insertable into the body.

In some instances, a depression may be provided at the top of the cap. The depression may follow the portion of the cap that is inserted into the body. In some instances, a hollow or depression may be provided in the cap. The depression may be capable of accepting a portion of a channel that may be used to deliver a sample to the sample vessel. The depression may assist with guiding the channel to a desired portion of the cap. In one example, the channel may be positioned within the depression prior to bringing the channel and interior of the sample vessel into fluid communication.

Optionally, the channel and cap may be pressed together so that the channel penetrates the cap and enters the interior of the sample vessel, thereby bringing the channel and interior of the sample vessel into fluid communication. In some instances, the cap may have a slit through which the channel passes. Alternatively, the channel may poke through uninterrupted cap material. The channel may be withdrawn from the sample vessel, thereby bringing the channel and sample vessel out of fluid communication. The cap may be capable of resealing when the channel is removed. For the example, the cap may be formed of a self-healing material. In some instances, the cap may have a slit that may close up when the channel is removed, thereby forming a fluid tight seal.

In some embodiments, the body may include one or more flange or other surface feature. Examples of surface features may include flanges, bumps, protrusions, grooves, ridges, threads, holes, facets, or any other surface feature. The flange and/or other surface feature may circumscribe the body. The flange and/or surface feature may be located at or near the top of the body. The flange and/or other surface feature may be located at the top half, top third, top quarter, top fifth, top sixth, top eighth, or top tenth of the body. The surface features may be useful for support of the sample vessel within a sample collection device. The surface features may be useful for removing the sample vessel from the sample collection device and/or positioning the sample vessel within the sample collection device. The flange and/or other surface feature may or may not engage with the cap.

Optionally, the cap may have any dimension relative to the sample vessel body. In some instances, the cap and/or body may have similar cross-sectional areas. The cap may have the same or a substantially similar cross-sectional area and/or shape as the top of the body. In some instances, the cap may have a lesser length than the body. For example, the cap may have a length that may be less than 60%, 50%, 40%, 30%, 25%, 20%, 15%, 10%, 7%, 5%, 3% or 1% of the length of the body.

Figures 1C, 1D, 1E:
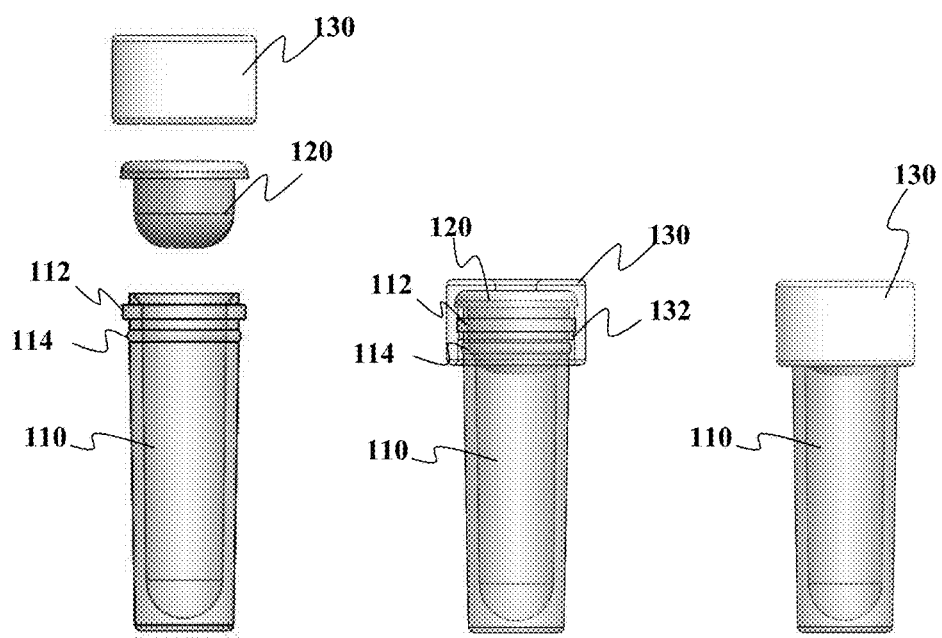

Referring now to FIGS. 1C to 1E, a still further embodiment of sample vessel 100 may include a cap holder 130 that fits over the cap to hold the cap in place. By way of non-limiting example, the cap holder 130 may also include an opening in the cap holder 130 that allows for a member such as an adapter to slide through and penetrate the cap 120. FIG. 1C shows the parts in an exploded view.

FIG. 1D shows a cross-section view showing one embodiment wherein the sample vessel body 110 having a cap 120 covered by a cap holder 130. As seen in FIG. 1D, the cap holder 130 has a locking feature 132 for securing the cap holder 130 to the sample vessel body 110 and/or the cap 120. In one embodiment, the locking feature 132 comprises an interior ridge which will engage one or more of the ridges 112 and 114 on the sample vessel body 110. FIG. 1E shows a side view of the cap holder 130 coupled to the sample vessel body 110.

In some instances, a surface (interior and/or exterior) of the sample vessel may be coated and/or treated with a material. For example, an interior surface of the sample vessel may be coated with fixatives, antibodies, optical coatings, anticoagulant, and/or preservatives. These may be the same or different from any material coatings in the channels. In one non-limiting example, the coating may be but are not limited to polytetrafluoroethylene, poly-xylene, or other material as a treatment for surfaces to reduce the surface tension.

Optionally, the coating is applied on all interior surfaces of the sample vessel. Optionally, some embodiments may apply the coating in a pattern covering only select areas in the sample vessel. Some embodiments may only cover upper interior regions of the sample vessel. Optionally, some may cover only lower interior regions of the sample vessel. Optionally, some may cover strips, lanes, or other geometric patterns of the interior regions of the sample vessel. Optionally, some embodiments may also coat the surfaces of the cap, plug, or cover that is used with the sample vessel. Some embodiments may have the surfaces where sample enters the sample vessel to be coated to provide for a smooth transfer of sample away from the entry area and towards a destination site such as but not limited to a bottom portion of the container.

Optionally, the coating may be a wet or dry coating. Some embodiments may have at least one dry coating and at least one wet coating. In some instances one or more reagents may be coated and dried on the interior surface of the sample vessel. The coating may alternatively be provided in a moist environment or may be a gel. Some embodiments may include a separator gel in the sample vessel to keep select portions of the sample away from other portions of the sample. Some embodiments may include serum separator gel or plasma separator gel such as but not limited to polyester-based separator gels available from Becton Dickinson.

Optionally, one or more solid substrates may be provided within the sample vessel. For example, one or more beads or particles may be provided within the sample vessel. The beads and/or particles may be coated with reagents or any other substance described herein. The beads and/or particles may be capable of dissolving in the presence of the sample. The beads and/or particles may be formed from one or more reagents or may be useful for treating the sample. A reagent may be provided in a gaseous form within the sample vessel. The sample vessel may be sealed. The sample vessel may remain sealed before the sample is introduced into the sample vessel, after the sample has been introduced to the sample vessel, and/or while the sample is being introduced into the sample vessel. In one embodiment, the sample vessels may have smooth surfaces and/or round bottoms. This is helpful to minimize the stress on the blood sample, especially during centrifugation. Of course, in alternative embodiments, other shapes of the bottom of the sample vessel are not excluded.

Figure 1F:

FIG. 1F further shows that the sample vessels may each have at least one information storage unit associated with the sample vessels. Optionally, some embodiments may have one information storage unit convey information about a plurality of sample vessels, particularly (but not exclusively) in cases where the sample vessels all contain sample from the same subject. Such an information storage unit could be on the carrier that holds the multiple sample vessels, instead of being on the sample vessels themselves.

Figure 1G:
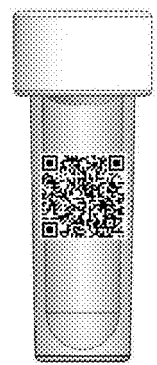

FIG. 1F shows a bottom-up view of an underside of one of the sample vessels that in one nonlimiting example, the information storage unit 160 may be at least one of: a barcode (e.g., 1-D, 2-D, or 3-D), quick response (QR) code, image, shape, word, number, alphanumeric string, color, or any combination thereof, or any type of visual information storage unit. Others may use information storage units that are not in the visible spectrum. Others may use RFID tags, RF information storage units, IR emitting tags, or other markers that do not rely on identification through signals sent through the visual spectrum. Of course, the information storage unit 160 may also be positioned to be on a top end surface of the sample vessel. FIG. 1G shows that, optionally, an information storage unit 160 may also be included on a side surface of the sample vessel. This may be in addition to or in place of the top or bottom positioned information storage unit(s) 160.

In one non-limiting example, information storage unit 160 may be used to identify sample and/or types of sample in a sample collection device. Optionally, there may be one or more information storage units per sample vessel. Some may also use information storage units on the sample vessel holders. Information storage units may identify the sample collection device, one or more individual sample vessels within the device, or components of the device. In some instances, the sample collection device, a portion of the sample collection device, and/or the sample vessels may be transported. In one example, the sample collection device or a portion of the sample collection device, may be transported via a delivery service, or any other service described elsewhere herein. The sample vessel may be delivered so that one or more tests may be performed on the sample.

Optionally, the sample identity and/or the identity of the individual who provided the sample could be tracked. By way of non-limiting example, information associated with the individual or individuals (e.g., name, contact information, social security number, birth date, insurance information, billing information, medical history) and other information of who provided the sample may be included. In some instances, the type of sample (e.g., whole blood, plasma, urine, etc.) may be tracked. Optionally, the types of reagents that the sample will have encountered (e.g., anticoagulants, labels, etc.) could also be tracked. Additional information about the sample collection, such as date and/or time of collection, circumstances under which sample was collected, types of tests to be run on the sample, setting(s) for the tests, test protocols, insurance information, medical records information, or any other type of information may be considered.

In at least one or more embodiments described herein, information storage units may assist with tracking such information. The information storage units may be associated with such information. Such information may be stored off-board the sample collection device, on-board the sample collection device, or any combination thereof. In some instances, the information may be stored on one or more external devices, such as servers, computers, databases, or any other device having a memory. In some instances, the information may be stored on a cloud computing infrastructure. One or more resources that store the information may be distributed over the cloud, through the internet from a remote server, wireless to a remote computer processor, or the like. In some instances, a peer-to-peer infrastructure may be provided. The information may be stored in the information storage unit itself, or may be associated with the information storage unit elsewhere, or any combination thereof.

Optionally, an information storage unit may provide unique identification, or may provide a high likelihood of providing unique identification. In some instances, the information storage unit may have a visible component. The information storage unit may be optically detectable. In some instances, the information storage unit may be discernible using visible light. In some examples, the information storage unit may be a barcode (e.g., 1-D, 2-D, or 3-D), quick response (QR) code, image, shape, word, number, alphanumeric string, color, or any combination thereof, or any type of visual information storage unit.

In other embodiments, the information storage unit may be optically detectable via any other sort of radiation. For example, the information storage unit may be detectable via infrared, ultraviolet, or any other type of wavelength of the electromagnetic spectrum. The information storage unit may utilize luminescence, such as fluorescence, chemiluminescence, bioluminescence, or any other type of optical emission. In some instances, the information storage unit may be a radio transmitter and/or receiver. The information storage unit may be a radiofrequency identification (RFID) tag. The information storage unit may be any type of wireless transmitter and/or receiver. The information storage unit may send one or more electrical signal. In some instances, GPS or other location-related signals may be utilized with the information storage unit.

Optionally, an information storage unit may be and/or include an audio component or acoustic component. The information storage unit may emit a sound that may be discernible to uniquely identify the identified component.

Optionally, the information storage unit may be detectable via an optical detection device. For example, a bar code scanner may be capable of reading the information storage unit. In another example, a camera (e.g., for still or video images) or other image capture device may be capable of capturing an image of the information storage unit and analyzing the image to determine the identification.

Optionally, the information storage units may be on the holder of the sample vessel(s). One or more indentation may be provided in the holder. The information storage unit may be located within the indentation. The indentations may be on the bottom or side surface of the holder. In some embodiments, the holder may include one or more protrusion. The information storage unit may be located on the protrusion. In some instances, the information storage units may be provided on an exterior surface of the holder. The information storage units may alternatively be positioned on an interior surface of the holder. The information storage units may be detected from outside the sample collection device.

In some embodiments, the information storage units may be on an exterior surface of the sample vessels or an interior surface of the sample vessels. The information storage units may be detectable from outside the sample vessels. In some embodiments, the information storage units may be provided on a bottom surface of the sample vessels.

In one non-limiting example, the holder may include an optically transmissive portion. The optically transmissive portion may be on a bottom of the holder or a side of the holder. For example, a transparent or translucent window may be provided. In another example, the optically transmissive portion may be a hole without requiring a window. The optically transmissive portion may permit a portion inside the holder to be visible. The information storage units may be provided on an exterior surface of the holder on the optically transmissive portion, an interior surface of the holder but may be visible through the optically transmissive portion, or on an exterior or interior surface of the sample vessel but may be visible through the optically transmissive portion. In some instances, the information storage unit may be provided on an interior surface of the sample vessel, but the sample vessel may be optically transmissive so that the information storage unit is viewable through the sample vessel and/or optically transmissive portion.

Optionally, the information storage unit may be a QR code, bar code, or other optical information storage unit that may be optically visible, such as but not limited to being visible from outside the sample collection device. A QR code may be visible through an optical window, hole, or the like at the bottom of the holder of the sample collection device. The QR code may be provided on the sample collection device holder or on a portion of the sample vessel visible through the holder. An image capturing device, such as a camera or scanner may be provided external to the sample vessels or the transport container, and may be capable of reading the QR code.

In some embodiments, a single or a plurality of QR codes or other information storage units may be provided on a sample collection device. In some instances, each sample vessel may have at least one information storage unit, such as a QR code associated with it. In one example, at least one window may be provided in a holder per sample vessel, and each window may permit a user to view a QR code or other information storage unit. For example, two sample vessels may be housed within a holder, each of the sample vessels having an associated information storage unit discernible from outside the holder.

In some embodiments, the information storage units may be provided with sample vessels housed by the holder. Separating the holder from the rest of the sample collection device may cause the sample vessels to be separated from the rest of the sample collection device. The sample vessels may remain within the holder or may be removed from the holder. The information storage units may remain with the sample vessels even if they are removed from the holder. Alternatively, the information storage units may remain with the holder even if sample vessels are removed. In some instances, both the holder and sample vessels may have information storage units so that the sample vessels and holders may be individually tracked and/or matched even when separated.

In some instances, any number of sample vessels may be provided within the sample collection device. Some embodiments may connect all of these sample vessels to the sample collection device all at once. Optionally, the sample vessels may be coupled in a sequential or other non-simultaneous manner. The sample vessels may be capable of receiving sample received from a subject. Each sample vessel may optionally have a unique information storage unit. The unique information storage unit may be associated with any information relating to the sample, subject, device, or component of the device.

In some instances, each information storage unit for each sample vessel may be unique or contain unique information. In other embodiments, the information storage unit on the sample vessel need not be unique. Optionally, some embodiments may have information unique for the device, for the subject, and/or for the type of sample. In some embodiments, the information on the information storage unit may be used to associate several sample vessels with the same subject or the same information.

Transport Container

Figures 2A, 2B:
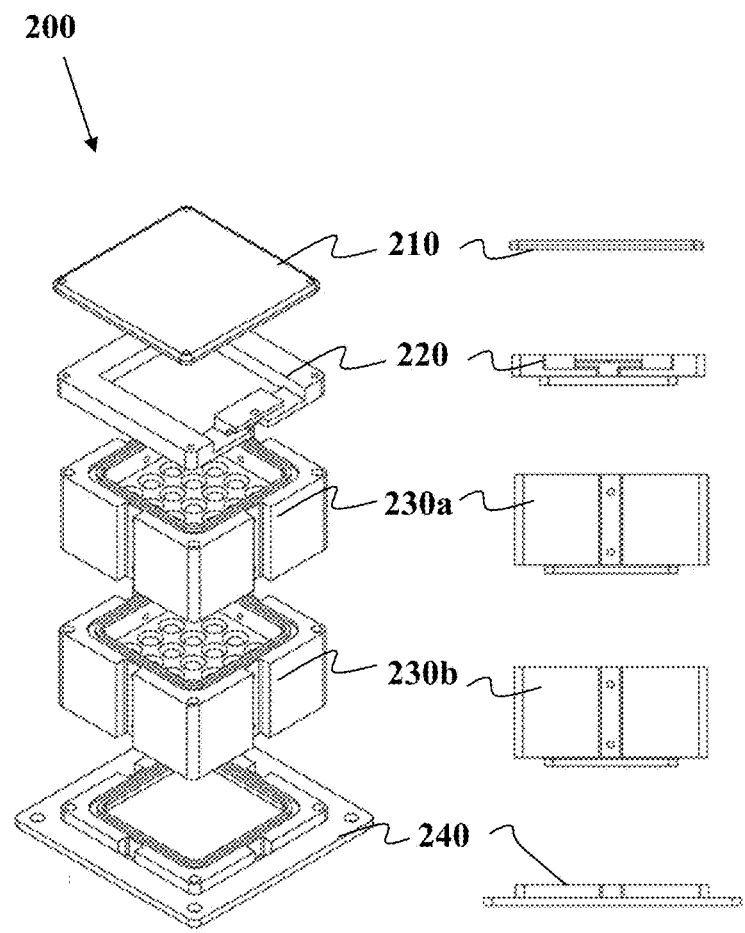

Referring now to FIGS. 2A-2B, an exploded perspective view is shown of one non-limiting example of a transport container 200 provided in accordance with one embodiment described herein. It should be understood that the transport container 200 may be configured to have one or more features of any other container described elsewhere herein. By way of non-limiting example, the transport container 200 may be useful for transporting one or more sample vessels therein. In some embodiments, the transport container 200 provides a thermally controlled interior area to minimize undesired thermal decomposition of the sample during transport to another location, such as but not limited to an analysis facility. It should be understood that the transport container may be placed inside one or more other containers during transport.

In one embodiment, the sample vessels may be provided from a sample collection device that collected the bodily fluid sample. By way of non-limiting example, the sample vessels may contain sample therein in liquid form. In most embodiments, liquid form also includes embodiments that are suspensions.

By way of non-limiting example, the transport container 200 may have any dimension. In some instances, the transport container 200 may have a total volume of less than or equal to about $1 \text{ m}^3$, $0.5 \text{ m}^3$, $0.1 \text{ m}^3$, $0.05 \text{ m}^3$, $0.01 \text{ m}^3$, $1000 \text{ cm}^3$, $500 \text{ cm}^3$, $300 \text{ cm}^3$, $200 \text{ cm}^3$, $150 \text{ cm}^3$, $100 \text{ cm}^3$, $70 \text{ cm}^3$, $50 \text{ cm}^3$, $30 \text{ cm}^3$, $20 \text{ cm}^3$, $15 \text{ cm}^3$, $10 \text{ cm}^3$, $7 \text{ cm}^3$, $5 \text{ cm}^3$, $3 \text{ cm}^3$, $2 \text{ cm}^3$, $1.5 \text{ cm}^3$, $1 \text{ cm}^3$, $700 \text{ mm}^3$, $500 \text{ mm}^3$, $300 \text{ mm}^3$, 100 mm³, 50 mm³, 30 mm³, 10 mm³, 5 mm³, or 1 mm³. The footprint and/or a largest cross-sectional area of the transport container may be less than or equal to about 1 m², 0.5 m², 0.1 m², 0.05 m², 100 cm², 70 cm², 50 cm², 30 cm², 20 cm², 15 cm², 10 cm², 7 cm², 5 cm², 3 cm², 2 cm², 1.5 cm², 1 cm², 70 mm², 50 mm², 30 mm², 10 mm², 5 mm², or 1 mm². In some instances, the transport container may have a dimension (e.g., height, width, length, diagonal, or circumference) of less than or equal to about 1 m, 75 cm, 50 cm, 30 cm, 25 cm, 20 cm, 15 cm, 12 cm, 10 cm, 9 cm, 8 cm, 7 cm, 6 cm, 5 cm, 4 cm, 3 cm, 2 cm, 1 cm, 0.7 cm, 0.5 cm, 0.3 cm, or 1 mm. In some instances, the largest dimension of the transport container may be no greater than about 1 m, 75 cm, 50 cm, 30 cm, 25 cm, 20 cm, 15 cm, 12 cm, 10 cm, 9 cm, 8 cm, 7 cm, 6 cm, 5 cm, 4 cm, 3 cm, 2 cm, 1 cm, 0.7 cm, 0.5 cm, 0.3 cm, or 1 mm.

Optionally, the transport container may be lightweight. In some embodiments, the transport container may weigh less than or equal to about 10 kg, 5, kg, 4 kg, 3 kg, 2 kg, 1.5 kg, 1 kg, 0.7 kg, 0.5 kg, 0.3 kg. 100 g, 70 g, 50 g, 30 g, 20 g, 15 g, 10 g, 7 g, 5 g, 3 g, 2 g, 1 g, 500 mg, 300 mg, 200 mg, 100 mg, 70 mg, 50 mg, 30 mg, 10 mg, 5 mg, or 1 mg, with or without the sample vessels having sample therein.

As seen in FIGS. 2A and 2B, one embodiment of the transport container may have a top cover 210, a housing for a thermal regulating device 220, one or more insert trays for the transport containers 230a, 230b, and a bottom plate 240.

In one embodiment, the top cover 210 has a substantially flat shape although other shapes are not excluded. The top cover 210 may cover a thermal regulating device such as but not limited to heater or cooler contained in the transport container. The top cover may or may not have the same footprint as a housing 220 for the thermal regulating device. A cooler, heater, or other thermal regulating device 220 may be provided within the transport container 200. Optionally, the device 220 may be active or passive units. The thermal regulating device may keep the sample vessels within the transport container 200 at a desired temperature or below a predetermined threshold temperature. Optionally, the thermal regulating device may be any temperature control unit known in the art. Optionally, the thermal regulating device may be capable of heating and/or cooling. Optionally, the thermal regulating device may be a thermoelectric cooler. Optionally, the thermal regulating device may be encased between the top cover and the housing for the cooler.

Optionally, the top cover and the housing may or may not form an airtight seal. The top cover and/or housing may be formed from a material with a desired thermal conductivity. For example, the housing 220 may have a selectable thermal conductivity. In one embodiment, the housing may include an embedded phase change material (PCM) within the box material, so the temperature is substantially uniform throughout. PCM holds a very good temperature profile. It is desirable not to have supercooling of the sample, such as that associated with ice, which may create a negative drop to −5° C. PCM can be configured to control to temperature ranges above freezing. By way of nonlimiting example, thermal conductivity may be in the range between about 100-250 W/m/K (watts/meter/Kelvin). Optionally, each sample vessel will come into contact with the PCM. Some embodiments may have one PCM for each layer. The PCM material may be flow molded into the container material. Optionally, gaps in the tray may be filled with PCM. The PCM can provide a passive thermal control technique.

Optionally, the PCM may be incorporated into the injection molding material. In such an embodiment, the entire container may be a cooling medium. This can also prevent leakage of PCM from chambers in the container. Container size can also shrink when the PCM is directly integrated into the container material. Energy density is greater since storage capacity per mass is increased. Mixing plastics with PCM material can be configured to have both strength and cooling. By way of non-limiting example, 30% of the material may be PCM and the remainder is plastic for rigidity. By way of non-limiting example, between 20% to 40% of the material may be PCM while the remainder is another material such as but not limited to plastic for mechanical rigidity. Some embodiments may use a blow-molded outer that is filled with PCM or other material. Inner could be formed with a different technique as it is may not be critical for the interior to be cosmetically appealing. Optionally, cast molding or other lower temperature molding process could also be used in place of or in combination with injection molding of the PCM integrated container material. Embedded PCM could also be in the trays. Some embodiments could be a tray that is much more thermally conductive to achieve even, uniform cooling profile.

In one embodiment, the transport container 200 may also have each of the trays 230a and 230b configured so that any information storage units on the sample vessels are easily readable without having to remove the sample vessels from the trays 230a and 230b. In one example, the holders have openings at the bottom that allow information storage units on the bottom to be visualized while the sample vessels are still in the trays 230a and 230b.

Figure 3:
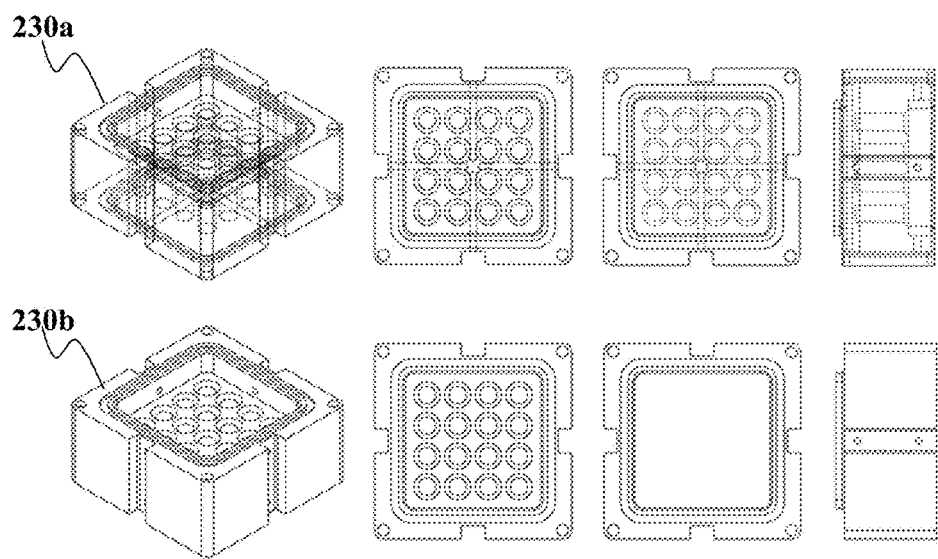

FIG. 3 shows a plurality of views of the transport container 200. Some show that the sample vessel holders in the trays 230a or 230b may have open bottoms such that any information storage unit, such as but limited to a barcode or other information storage unit, can be read from underneath or other orientation that does not require that sample vessels be removed from the transport container 200. Optionally, only certain portions of the transport container 200 such as but not limited to a layer, a tray, or the like is removed to obtain the desired information. Optionally, bar codes or other information storage units can be accessed through one or more openings in the tray. That allows for bar code scanning of very small transport container. Optionally, one could scan rows of sample vessels individually or can scan entire tray all at once. Optionally, a user can see all sample vessel holders. Optionally, a computer vision system can also scan to see if a step such as centrifugation was completed. This can be at either end of the shipping process. The computer vision system can visualize the sample vessel and determine if the sample there is in a form that confirms that a desired step was completed. If it detects an error, the system can inform the user or the system of the issue and/or re-perform the missing and/or incorrectly performed step. Optionally, the holders may have closed bottoms and information may be on the sides or other surfaces of the transport container 200.

In some embodiments, the shapes of the holders may also be designed to follow the contours of the sample vessels 134 therein to increase surface area contact and improve thermal control of the sample vessels. Optionally, thermal control of the sample vessels may occur through thermal transfer with tray and/or the PCM, but not in direct contact with the PCM. Optionally, some sample vessels 134 could also be in direct contact with the container and/or the PCM. The openings for the sample vessels and/or the holders may be in linear rows, in a honeycomb pattern, or be in another pattern.

Figures 4A, 4B:
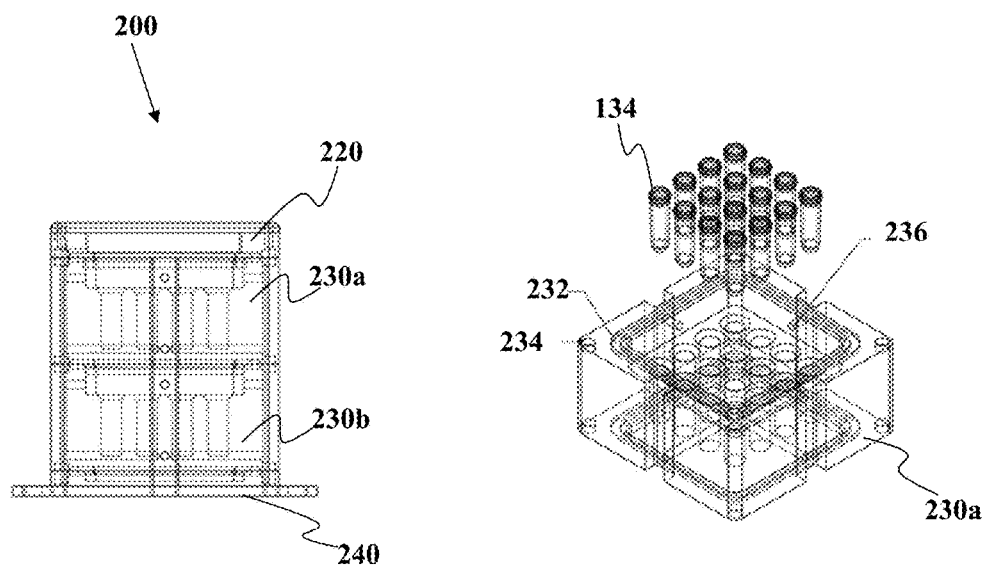
FIGS. 4A-4C show schematics of various embodiments described herein.

Referring now to FIGS. 4A and 4B, a transport container 200 is shown fully assembled. FIG. 4B shows a plurality of sample vessels 134 such as those associated with the sample collection device. The sample vessels 134 can all be from sample associated with one subject in which case an information storage unit associated with tray 230a can be used to provide information about this group of samples. Optionally, individual sample vessels may still each have an information storage unit that is the same as that of the tray 230a or they may each be unique. Some embodiments may insert sample vessels from multiple subjects into the same tray 230a. Optionally, some may only partially fill each tray. Some may fill each opening in the tray, but not every sample vessel will have sample therein (i.e. some may be empty sample vessels inserted to provide uniform thermal profile). These stackable trays 230a may have closure devices that use elements such as but not limited to magnets, mechanical latches, or other coupling mechanisms to couple trays together. In some embodiments, magnets may be used to engage the tray holding the sample vessels to enable ease of opening during automation of loading and unloading. Optionally, the user cannot remove the tray from the container. Optionally, the user cannot remove the tray from the container without the use of a tool to release the tray. Some embodiments have a keying mechanism (magnetic or other technique). In this manner, the patient service center can put sample in but cannot take it out. Optionally, some embodiments can have shaped openings selected so that one cannot put the sample vessels and/or their holders in the wrong way to prevent user error.

In one embodiment, the loading and/or unloading may occur in a temperature regulated room or chamber to maintain samples in a desired temperature range. In one embodiment, it is desirable to have a temperature range between about 1° to 10° C. Optionally, it is desirable to have the temperature range between about 2° to 8° C. Optionally, it is desirable to have a temperature range between about 4° to 5° C. Optionally, the materials of the trays 230a and 230b may be used to provide thermally controlled atmosphere for the sample vessels. Some use convection to control thermal profile inside the transport container 200.

FIG. 4B also shows that in this particular embodiment, there may be a groove 232 for an o-ring or other seal that can provide a tight connection between layers of the transport container. The system may also include closure mechanisms 234 such as but not limited magnetic closure devices to maintain the stackable insert tray in the desired position. It should also be understood that some embodiments may have through-holes 236 for wiring sensor(s) to detect conditions experienced the stackable insert tray during shipment.

Figure 4C:
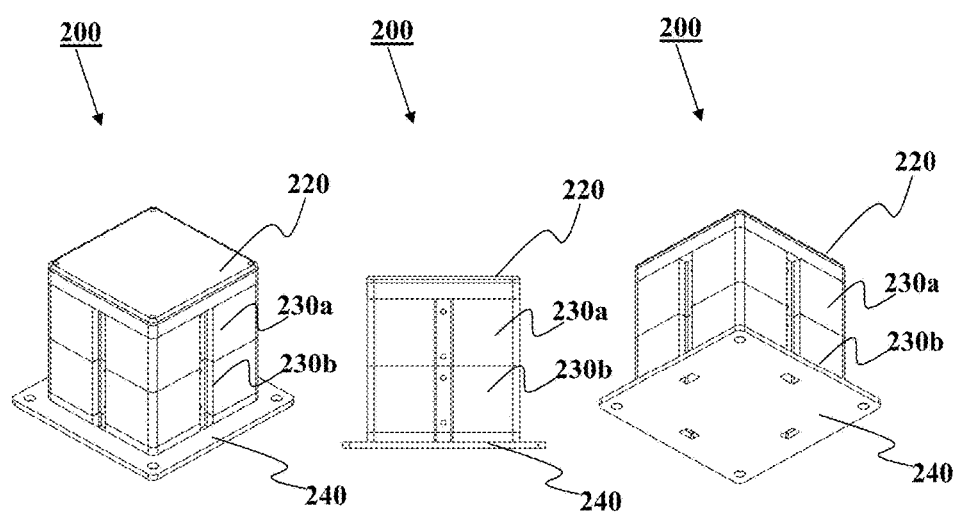

FIG. 4C shows various perspective views of the embodiment of FIGS. 4A and 4B when the various components such the stackable trays and the lids are joined together to form the transport container 200. As seen in FIG. 4C, the shipping container may be comprised of multiple layers of sample vessels. Optionally, some embodiments may have only a single layer of sample vessels. Some embodiments may use actively cooling or thermal control in one or more layers of the transport container 200. By way of non-limiting example, one embodiment may have a thermo-electric cooler in the top layer. Optionally, some embodiments may use a combination of active and passive thermal control. By way of non-limiting example, one embodiment may have a thermal mass such as but not limited to a phase change material (PCM) that is already at a desired temperature. An active thermal control unit may be included to keep the PCM in the desired temperature range. Optionally, some embodiments may use only a thermal mass such as but not limited to a PCM to maintain temperature in a desired range.

Transport Container with Removable Tray

Figure 5:
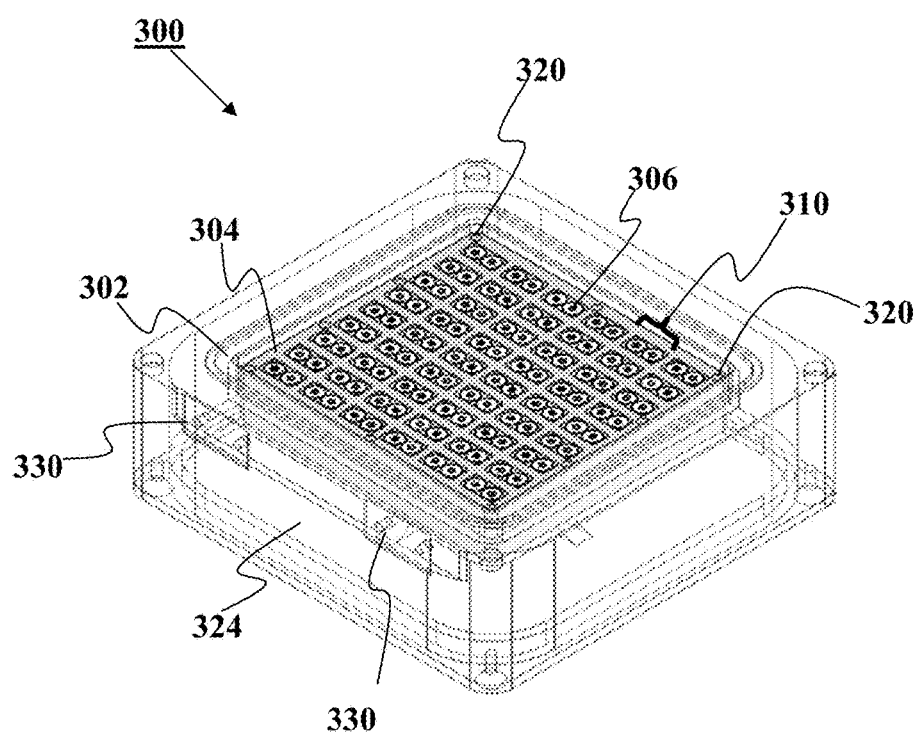
FIG. 5 shows a perspective view of one portion of a sample transport container having a plurality of sample vessels therein according to at least one embodiment described herein.

Referring now to FIG. 5, yet another embodiment of a transport container will now be described. FIG. 5 shows a transport container 300 having a thermally-controlled interior 302 that houses a tray 304 that can hold a plurality of sample vessels 306 in an array configuration, wherein each of the vessels 306 holds a majority of its sample in a free-flowing, non-wicked form and wherein there is about 1 ml or less of sample fluid in each of the vessels. Optionally, there is about 2 ml or less of sample fluid in each of the vessels. Optionally, there is about 3 ml or less of sample fluid in each of the vessels. In one non-limiting example, the vessels are arranged such that there are at least two vessels in each transport container with sample fluid from the same subject, wherein at least a first sample includes a first anticoagulant and a second sample includes a second anticoagulant in the matrix.

Although FIG. 5 shows the sample vessels 306 are held in an array configuration, other predetermined configurations are not excluded. Some may place the sample vessels into hinged, swinging, or other retaining mechanism in the tray that may allow for motion in one or two degrees of freedom. Some embodiments may place the sample vessels into a device that has first configuration during loading and then assumes a second configuration to retain the sample vessels during transport. Some embodiments may place the sample vessels into a material that has first material property during loading and then assumes a second property such as but not limited to hardening to retain the sample vessels during transport.

In some embodiments, the sample vessels are in holders 310 and the tray 304 defines openings and/or cavities sized to fit the holders 310 and not the sample vessels. By way of non-limiting example, the holders 310 can be used to keep associated vessels 306 physically together while in the tray 304. Some embodiments have the holders 310 directly contacting the tray 304 so that the vessels are protected from direct contact with the tray 304. In one non-limiting example, the tray can hold at least 100 vessels, or optionally, at least 50 holders each having two vessels.

Referring still to FIG. 5, this embodiment of transport container 300 may have some retaining mechanism 320 such as but not limited to clips, magnetic areas, or the like to hold the tray 306. The retaining mechanism 320 may be configured to hold the tray 304 in a manner releasable when desired. Optionally, the retaining mechanism 320 may be configured to hold the tray 304 in an un-releasable manner. In the embodiment shown in FIG. 5, the retaining mechanism 320 is shown as magnetic and/or metallic members in tray 304 that are attracted to metal and/or magnetic members in the container 300. When the transport container 300 arrives at a processing facility, the tray 304 may be configured to be removed from the container 300. This can occur by use of one or more techniques including but not limited to using strong magnets to engage the magnetic and/or metallic members in tray 304. Some embodiments may use grippers, hooks, or other mechanical mechanisms to remove the tray 304 from the container 300. Some embodiments may use a combination of techniques to remove the tray 304. It should also be understood that some embodiments may opt to remove the vessels 306 and/or the holders 310 while the tray 304 remains in the container 300. Some techniques may perform at two or more of the foregoing techniques.

It should also be understood that the container 300 may itself be a cooling device, comprising a thermal control material such as but not limited to ice, a PCM, or the like. Other embodiments may directly integrate the thermal control material into the material used to form the container 300.

As seen in FIG. 5, some embodiments of the container 300 may have a substantial void space 324 in which one or more the thermal control material is housed or integrated therein.

Referring still to FIG. 5, the container 300 may also include openings 330 for attachment of hinges or other connection devices for covers or connections to other layers of the container 300. For ease of illustration, the cover and/or connections to the cover or other layer are not shown in FIG. 5. Although some embodiments may only use a single layer, it should be understood that multi-layer embodiments are not excluded.

Figure 6:
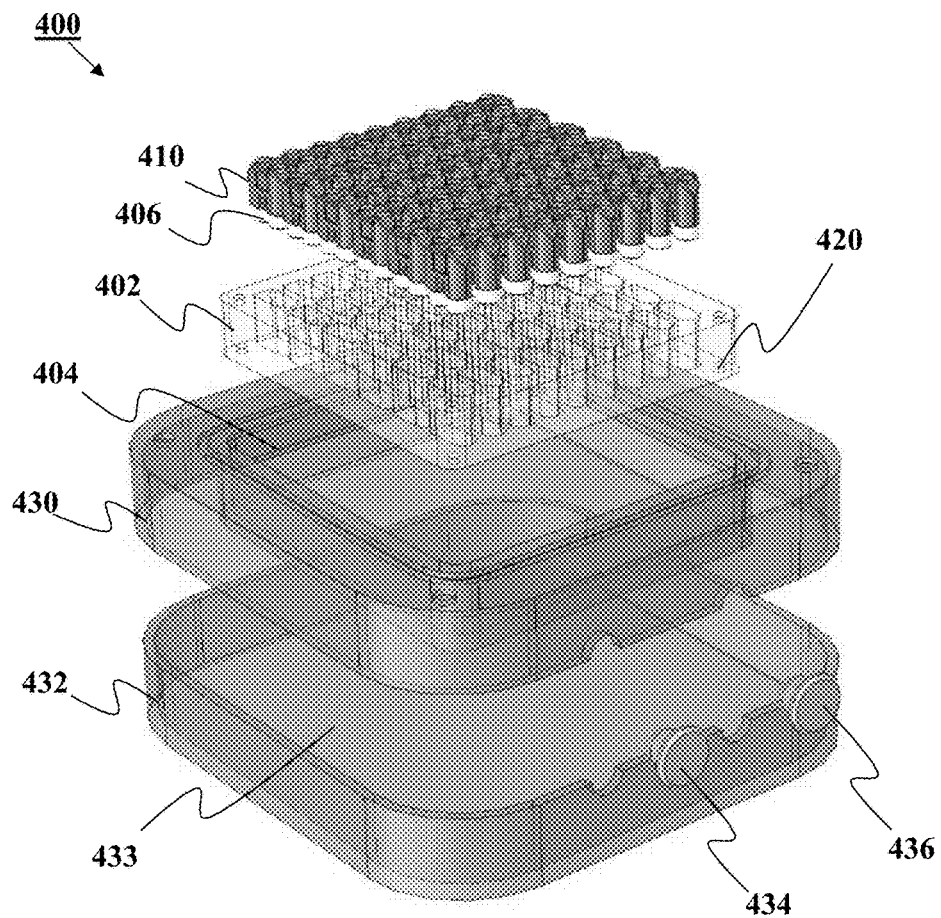
FIG. 6 is an exploded perspective view of one portion of a sample transport container having a plurality of sample vessels therein according to at least one embodiment described herein.

Referring now to FIG. 6, an exploded perspective view of yet another embodiment of a container 400 will now be described. The embodiment of FIG. 6 is designed to hold a tray 402 in the container interior 404. The exploded perspective view shows a plurality of vessels 406 in holders 410 in a tray 402. The tray 402 may be configured to have some or all portions of the retention mechanism 420 similar to retention mechanisms 320 in the tray 402. It should also be understood that the tray 402 may have one or more cutouts, protrusions, or features to allow the tray 402 to be inserted into the interior in a limited number of pre-determined orientations. Some embodiments may be configured to only enable one orientation of the tray in the container. Some embodiments may be configured to only enable two possible orientations of the tray in the container.

FIG. 6 shows that in one embodiment, the container 400 may be formed from two separate pieces 430 and 432. Optionally, some embodiment may be formed from three or more pieces. Optionally, some embodiment may be a single piece. The pieces 430 and 432 can have openings that filled by plugs 434 and 436. The interior 438 of the container 400 can retain a thermal control material such as but not limited to ice, a phase change material, or the like. Other embodiments may directly integrate the thermal control material into the material used to form the container 400.

In one instance, the interior 433 of the piece 432 can be filled with a thermal control material such as but not limited to a PCM. Optionally, one embodiment could use an active thermal control material such as but not limited to a thermoelectric cooler to cool the interior.

Figure 7:
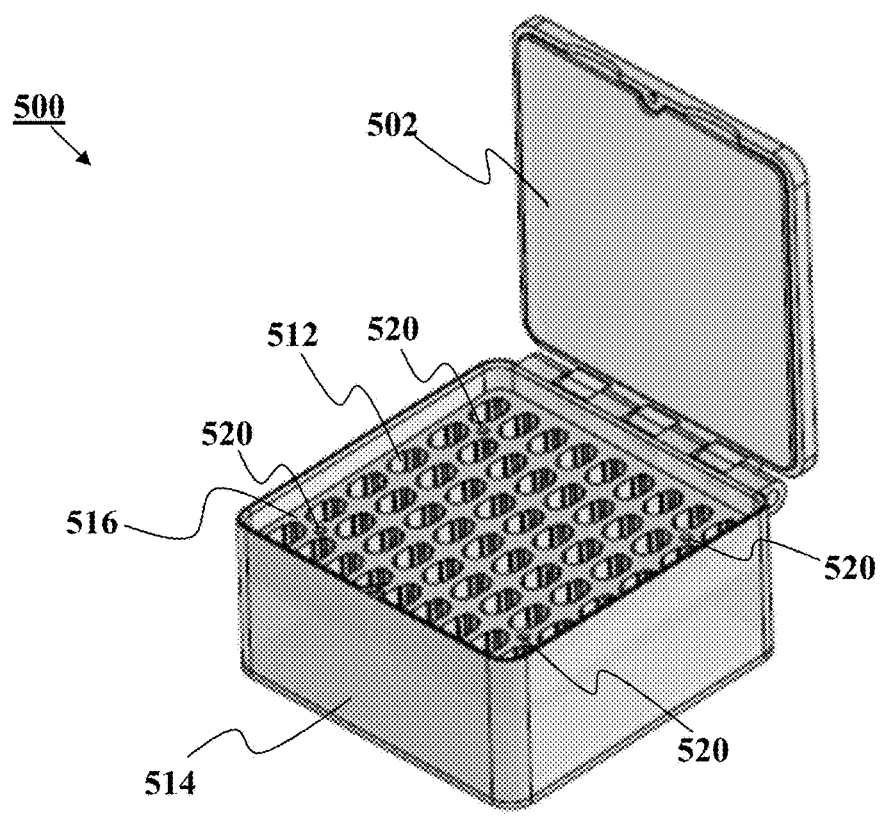
FIG. 7 shows a perspective view of a sample transport container according to yet another embodiment described herein.

Referring now to FIG. 7, yet another embodiment of the transport container 500 will now be described. FIG. 7 shows that the transport container 500 may include a lid 502 for covering the features and/or sample vessels therein. In some embodiments, the lid 502 may contain thermal insulating material. Optionally, the lid 502 may include a thermal control unit to assist in keeping the interior of the transport container 500 within a desired temperature range. Optionally, some embodiments may configure lid 502 to be a thermally conductive material that can be useful in keeping the interior of the container 500 within a desired temperature range through thermal transfer from an external thermal control source. By way of non-limiting example, the thermal control source may be a cooling source, a heating source, a thermoelectric heat exchanger, or other thermal control device. It should also be understood that similar thermal control source such as but not limited to a PCM or an active cooling device can also be included in the void space 514 below the layer 516.

It should be understood that the features 512 for retaining holders 310, 410, or other shaped holders for the vessels may be in a piece separate from the container or they can be integrally formed inside of the container. Optionally, the features 512 can be part of a tray such as the trays 302 and 402 shown in FIGS. 5 and 6. Such a tray can be fixed or removable from the container 500. Retaining mechanisms 520 may also be incorporated into the tray to allow it to be held in place during transport.

Sample Collection and Transport

Figure 8:
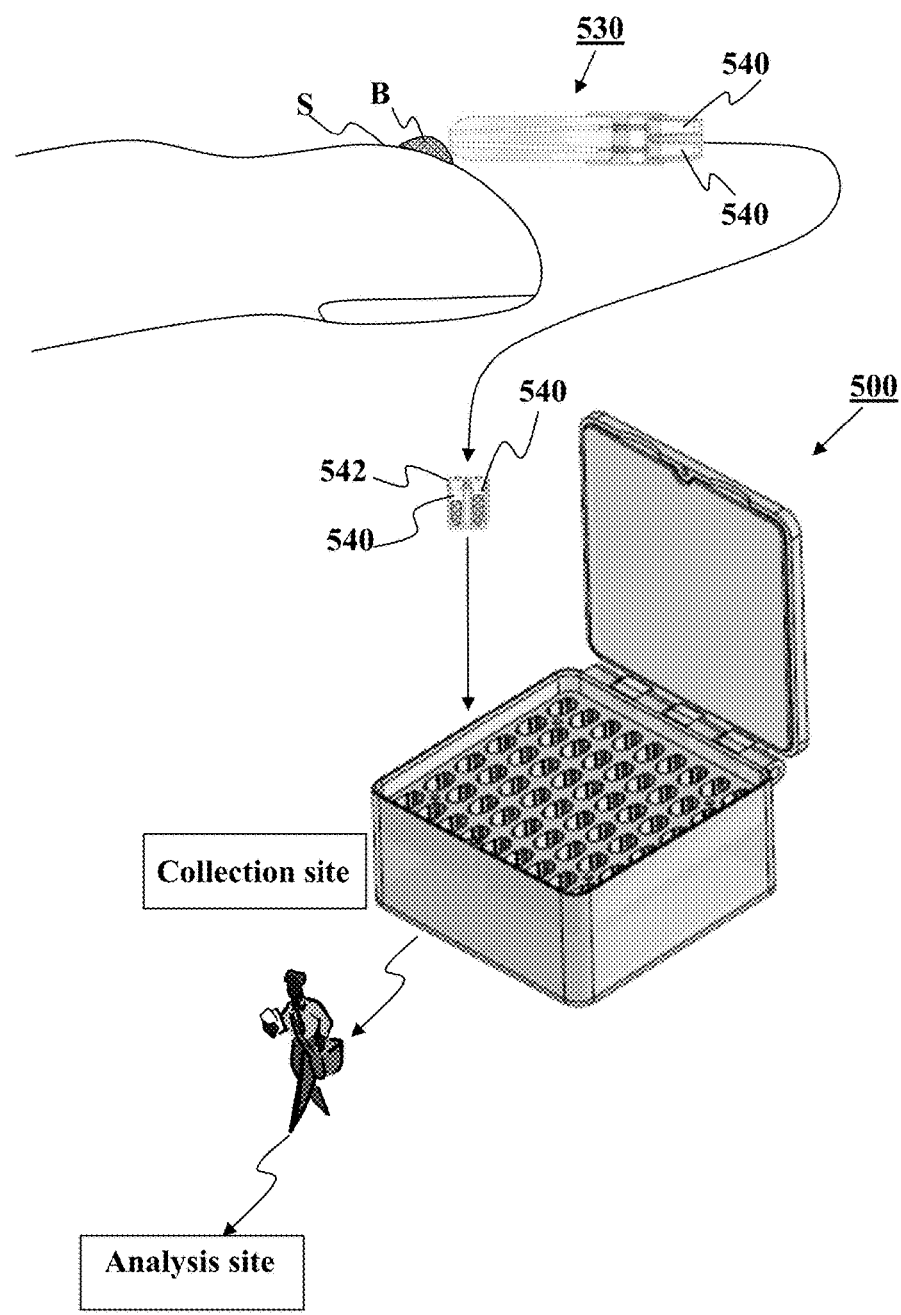
FIG. 8 shows a schematic of a sample collection and transport process according to one embodiment described herein.

Referring now to FIG. 8, one embodiment of bodily fluid sample collection and transport will now be described. FIG. 8 shows a bodily fluid sample B on a skin surface S of the subject. In the non-limiting example of FIG. 8, the bodily fluid sample B can be collected by one of a variety of devices. By way of non-limiting example, collection device 530 may be but is not limited to those described in U.S. Patent Application Ser. No. 61/697,797 filed Sep. 6, 2012, which is fully incorporated herein by reference for all purposes. In the present embodiment, the bodily fluid sample B is collected by one or more capillary channels and then directed into sample vessels 540. By way of non-limiting example, at least one of the sample vessels 540 may have an interior that is initially under a partial vacuum that is used to draw bodily fluid sample into the sample vessel 540. Some embodiments may simultaneously draw sample from the sample collection device into the sample vessels 540 from the same or different collection channels in the sample collection device. Optionally, some embodiments may simultaneous draw sample into the sample vessels In the present embodiment after the bodily fluid sample is inside the sample vessels 540, the sample vessels 540 in their holder 542 (or optionally, removed from their holder 542) are loaded into the transport container 500. In this embodiment, there may be one or more slots sized for the sample vessel holder 542 or slots for the sample vessels in the transport container 500. By way of non-limiting example, they may hold the sample vessels in an arrayed configuration and oriented to be vertical or some other pre-determined orientation. It should be understood that some embodiments of the sample vessels 540 are configured so that they hold different amount of sample in each of the vessels. By way of non-limiting example, this can be controlled based on the amount of vacuum force in each of the sample vessels, the amount of sample collected in the sample collection channel(s) of the collection device, and/or other factors. Optionally, different pre-treatments such as but not limited to different anti-coagulants or the like can also be present in the sample vessels.

As seen in FIG. 8, the sample vessels 540 are collecting sample at a first location such as but not limited to a sample collection site. By way of non-limiting example, the bodily fluid samples are then transported in the transport container 500 to a second location such as but not limited to an analysis site. The method of transport may be by courier, postal delivery, or other shipping technique. In many embodiments, the transport may be implemented by having a yet another container that holds the transport container therein. In one embodiment, the sample collection site may be a point-of-care. Optionally, the sample collection site is a point-of-service. Optionally, the sample collection site is remote from the sample analysis site.

Although the present embodiment of FIG. 8 shows the collection of bodily fluid sample from a surface of the subject, other alternative embodiments may use collection techniques for collecting sample from other areas of the subject, such as by venipuncture, to fill the sample vessel(s) 540. Such other collection techniques are not excluded for use as alternative to or in conjunction with surface collection. Surface collection may be on exterior surfaces of the subject. Optionally, some embodiments may collect from accessible surfaces on the interior of the subject. Presence of bodily fluid sample B on these surfaces may be naturally occurring or may occur through wound creation or other techniques to make the bodily fluid surface accessible.

Figure 9:
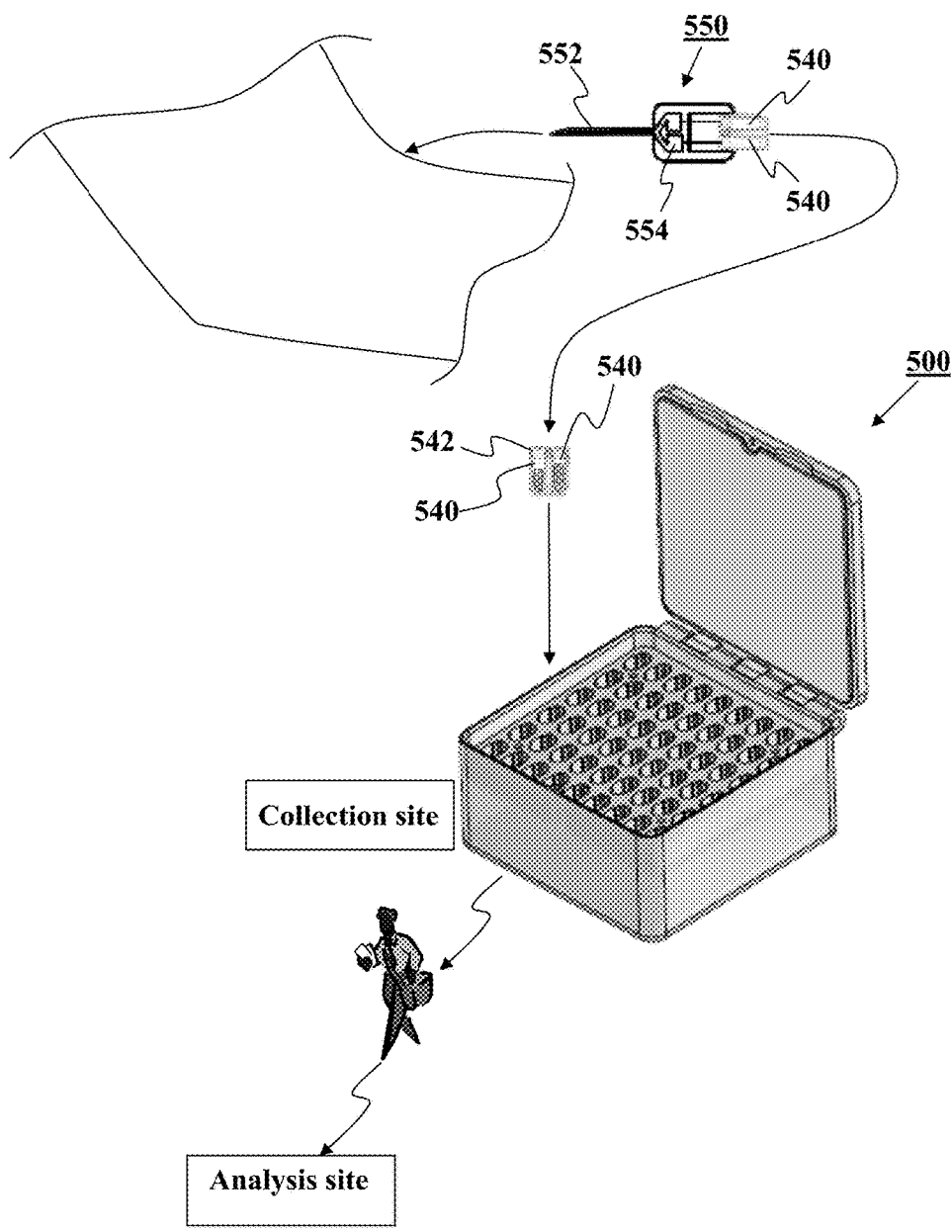
FIG. 9 shows a schematic of a sample collection and transport process according to yet another embodiment described herein.

Referring now to FIG. 9, yet another embodiment is described herein wherein bodily fluid sample can be collected from an interior of the subject versus collecting sample that is pooled on a surface of the subject. This embodiment of FIG. 9 shows a collection device 550 with a hypodermic needle 552 that is configured to collect bodily fluid sample such as but not limited to venous blood. In one embodiment, the bodily fluid sample may fill a chamber 554 in the device 550 at which time sample vessel(s) 540 may be engaged to draw the sample into the respective vessel(s). Optionally, some embodiments may not have a chamber 554 but instead have very little void space other than channel(s), pathway(s), or tube(s) used to direct sample from the needle 552 to the sample vessel(s) 540. For bodily fluid samples such as blood, the pressure from within the blood vessel is such that the blood sample can fill the chamber 554 without much if any assistance from the collection device. Such embodiments may optionally include one or more vents, such as but not limited to a port, to allow air escape as the channels in the collection device are filled with sample.

At least some or all of the embodiments can have a fill indicator such as but not limited to a view window or opening that shows when sample is present inside the collection device and thus indicate that it is acceptable to engage the sample vessel(s) 540. Optionally, embodiments that do not have a fill indicator are not excluded. The filled sample vessel(s) 540 may be disconnected from the sample collection device after a desired fill level is reached. Optionally, additional sample vessel(s) 540 can be engaged to the sample collection device 550 (or 530) to collect additional amounts of bodily fluid sample.

Figure 10:
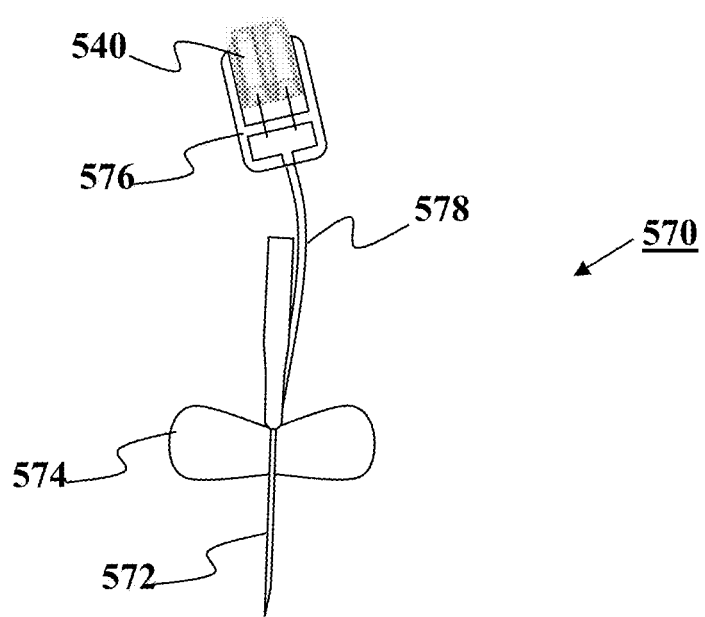
FIG. 10 shows a sample collection device according to one embodiment described herein.

FIG. 10 shows a still further embodiment of a sample collection device 570. This embodiment described herein has a tissue penetrating portion 572 such as but not limited to a hypodermic needle with a handling portion 574. The handling portion 574 can facilitate positioning of the tissue penetrating portion 572 to more accurately enter the patient to a desired depth and location. In the present embodiment, the sample collection vessel(s) 540 are in a carrier 576 that is not in direct physical contact with the tissue penetration portion 572. A fluid connection pathway 578 such as but not limited to a flexible tube can be used to connect the tissue penetrating portion 572 with the sample collection vessel(s) 540. Some embodiments have the sample vessel(s) 540 configured to be slidable to only be in fluid communication with the tissue penetrating portion 572 upon control of the user. At least some or all of the embodiments can have a fill indicator such as but not limited to a view window or opening that shows when sample is present inside the collection device and thus indicate that it is acceptable to engage the sample vessel(s) 540. Optionally, embodiments that do not have a fill indicator are not excluded. Some embodiments may optionally include one or more vents, such as but not limited to a port, to allow air escape as the channels in the collection device are filled with sample. In most embodiments, the filled sample vessel(s) 540 may be disconnected from the sample collection device after a desired fill level is reached. Optionally, additional sample vessel(s) 540 can be engaged to the sample collection device 570 to collect additional amounts of bodily fluid sample.

Sample Processing

Figure 11:
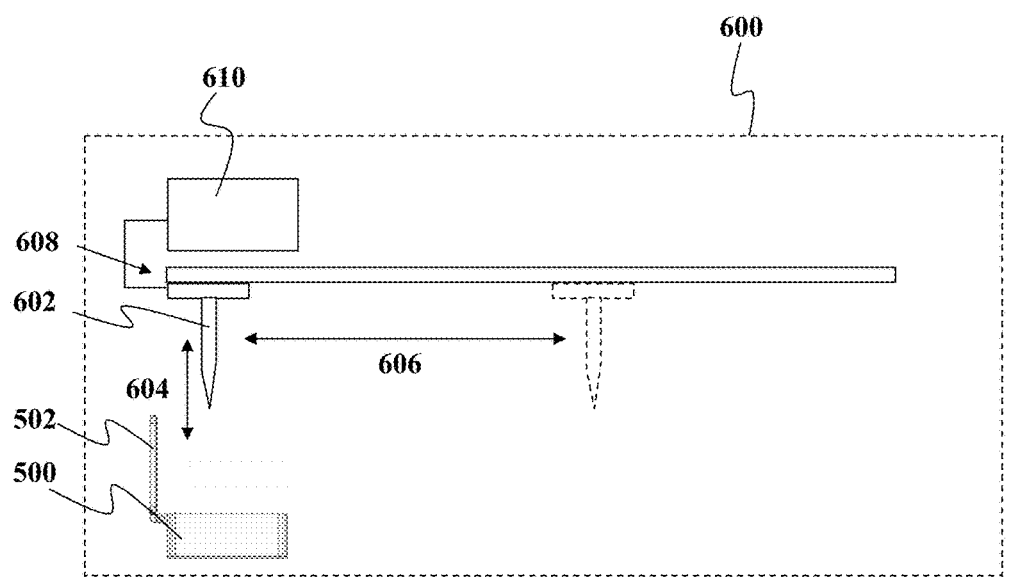
FIG. 11 shows a schematic view of one system for unloading sample vessels from a transport container according to one embodiment described herein.

Referring now to FIG. 11, a system view is shown of the transport container 500 having its contents unloaded after arriving at a destination location by unloading assembly 600. In one embodiment, after the lid 502 is positioned in an open position, the sample vessels in the container 500 can be removed from therein. By way of non-limiting example, the removal may occur by removing an entire tray of the sample vessels, removing holders of multiple sample vessels from the tray, and/or by removing the sample vessels individually. Some embodiments may use a robotically controlled structure 602 that can move vertically as indicated by arrow 604 and/or horizontally as indicated by arrow 606 along a gantry 608 to remove sample vessels from the container 500. A programmable process 610 can be used to control the position of the structure 602 that is used to manipulate the sample vessels. In one embodiment, the structure 602 includes a magnet for engaging the retention mechanisms to remove the tray from the structure 602. Other embodiments using robotic arms and/or other types of programmable manipulators can be configured for use herein and are not excluded.

By way of non-limiting example, the samples in the sample vessels can then be processed using systems such as that described in U.S. patent application Ser. No. 13/244,947 filed Sep. 26, 2011, fully incorporated herein by reference for all purposes. The analysis system can be configured in a CLIA compliant manner as described in U.S. patent application Ser. No. 13/244,946 filed Sep. 26, 2011, fully incorporated herein by reference for all purposes.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: in U.S. Provisional Patent Application No. 61/435,250, filed Jan. 21, 2011 ("SYSTEMS AND METHODS FOR SAMPLE USE MAXIMIZATION"), and U.S. Patent Publication No. 2009/0088336 ("MODULAR POINT-OF-CARE DEVICES, SYSTEMS, AND USES THEREOF").

While the above is a description of the embodiments as described herein, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2012 Theranos, Inc.

What is claimed is:

1. A method comprising:
    collecting a bodily fluid sample on a surface of a subject, wherein the collected sample is stored in one or more sample vessels each having an information storage unit on a bottom surface of each of the sample vessels;
    providing a transport container to house at least two or more sample vessels, wherein the vessels are arranged in a two-dimensional array configuration in the transport container and wherein the transport container further comprises a tray sized to fit inside the transport container and hold the sample vessels therein in the two-dimensional array configuration;
    arranging to have the sample vessels shipped in the transport container from a first location to a second location,
    wherein each of the sample vessels arrives at the second location holding a majority of its bodily fluid sample in a non-wicked, non-matrixed form that is removable from the sample vessels in liquid form and wherein the amount of sample in each of the sample vessels does not exceed about 2 ml;
    removing the tray from the transport container; and
    scanning information storage units on substantially all of the sample vessels, wherein the scanning occurs while the sample vessels remain in the tray in the two-dimensional array configuration at the second location;
    wherein the sample vessels held in slots in the tray, wherein said slots have open bottoms that allow said information storage units to be scanned from below after the tray is removed from the transport container.

2. The method of claim 1 wherein collecting comprises making at least one puncture on the subject to release the bodily fluid, wherein the puncture is not a venipuncture.

3. The method of claim 1 wherein collecting comprises using at least one lancet to make at least one puncture on the subject.

4. The method of claim 3 wherein the puncture is formed by pricking skin on a forearm of the subject.

5. The method of claim 1 wherein the sample vessel has an interior that is initially at sub-atmospheric pressure prior to drawing sample into the interior of the sample vessel.

6. The method of claim 5 wherein the sub-atmospheric pressure is selected to provide sufficient force to draw a desired volume of sample into the sample vessel.

7. The method of claim 1 wherein the transport container contains at least five or more sample vessels.

8. The method of claim 1 wherein the transport container is used to simultaneously ship bodily fluid samples from a plurality of different subjects.

9. The method of claim 1 wherein information associated with each of the sample vessels determines what tests will be run on the bodily fluid sample therein.

10. The method of claim 1 further comprising using a cooled tray to hold the sample vessels in a temperature controlled storage chamber prior to loading the vessels into the container and the same cooled tray is used to hold the sample vessels in the transport container, wherein the samples are placed into transport container with the cooled tray.

11. The method of claim 1 wherein sample vessels are arranged such that there are at least two vessels in each container with bodily sample fluid from the same subject, wherein at least a first sample includes a first anticoagulant and a second sample includes a second anticoagulant in the matrix.

12. The method of claim 1 the fluid sample comprises capillary blood for use in CLIA compliant laboratory testing.

13. The method of claim 1 further comprising using a housing providing a controlled-thermal-profile and high-heat-of-fusion material providing at least one cooling surface facing the sample vessels.

14. The method of claim 13 wherein the controlled-thermal-profile, high-heat-of-fusion material is embedded in material used to form the container.

15. The method of claim 1 further comprising scanning an information storage unit on each sample at a transport container receiving site and automatically placing the container into a cartridge.

16. The method of claim 1 further comprising using the same tray to hold sample vessels in an array configuration when in a refrigeration device prior to transport and when in the transport container.

17. The method of claim 16 wherein the tray comprises a plurality of slots having a shape to hold sample vessels holders in a preferential orientation, wherein the sample vessels cannot be inserted in a different orientation.

18. The method of claim 10 further comprising using a single step to load a plurality of sample vessels from cooled storage into the transport container while maintaining a desired sample-vessel-to-sample-vessel orientation during the loading step.

19. The method of claim 1 wherein the transport container has a first surface configured to define a preferential thermally-conductive pathway to a controlled-thermal-profile, high-heat-of-fusion material in the transport container.

* * * * *